US008882978B2

(12) United States Patent
Yada et al.

(10) Patent No.: US 8,882,978 B2
(45) Date of Patent: Nov. 11, 2014

(54) FAD-CONJUGATED GLUCOSE DEHYDROGENASE GENE

(71) Applicant: Ikeda Food Research Co., Ltd, Hiroshima (JP)

(72) Inventors: Takako Yada, Hiroshima (JP); Koji Miyamoto, Hiroshima (JP); Michinari Honda, Hiroshima (JP)

(73) Assignee: Ikeda Food Research Co., Ltd., Hiroshima (JP)

( * ) Notice: Subject to any disclaimer, the term of this patent is extended or adjusted under 35 U.S.C. 154(b) by 0 days.

(21) Appl. No.: 13/920,445

(22) Filed: Jun. 18, 2013

(65) Prior Publication Data

US 2014/0027280 A1   Jan. 30, 2014

Related U.S. Application Data

(62) Division of application No. 12/866,071, filed as application No. PCT/JP2007/063147 on Jun. 29, 2007, now Pat. No. 8,492,130.

(30) Foreign Application Priority Data

Jun. 29, 2006 (JP) ................. 2006-180491
Sep. 13, 2006 (JP) ................. 2006-247535

(51) Int. Cl.
| | |
|---|---|
| C12M 1/00 | (2006.01) |
| C12Q 1/54 | (2006.01) |
| C12N 9/00 | (2006.01) |
| C12N 9/96 | (2006.01) |
| C12N 1/20 | (2006.01) |
| C12N 15/00 | (2006.01) |
| G01N 33/66 | (2006.01) |
| C12Q 1/32 | (2006.01) |
| C12Q 1/00 | (2006.01) |
| C12N 9/04 | (2006.01) |

(52) U.S. Cl.
CPC ............ *C12Q 1/006* (2013.01); *C12Y 101/9901* (2013.01); *G01N 33/66* (2013.01); *C12Q 1/32* (2013.01); *C12N 9/0006* (2013.01); *G01N 2333/902* (2013.01)
USPC ........ 204/403.14; 435/14; 435/183; 435/188; 435/252.3; 435/320.1; 536/23.2

(58) Field of Classification Search
None
See application file for complete search history.

(56) References Cited

U.S. PATENT DOCUMENTS

| | | | |
|---|---|---|---|
| 5,286,362 A | 2/1994 | Hoenes et al. | |
| 6,100,037 A | 8/2000 | Phillips et al. | |
| 6,103,509 A | 8/2000 | Sode | |
| 6,338,790 B1 | 1/2002 | Feldman et al. | |
| 6,558,920 B1 | 5/2003 | Hata et al. | |
| 6,773,564 B1 | 8/2004 | Yugawa et al. | |
| 7,049,114 B1 | 5/2006 | Sode | |
| 7,067,295 B1 | 6/2006 | Sode | |
| 7,132,270 B2 | 11/2006 | Kratzsch et al. | |
| 7,244,600 B2 | 7/2007 | Sode et al. | |
| 7,553,649 B2 | 6/2009 | Tsuji et al. | |
| 8,492,130 B2 | 7/2013 | Yada et al. | |
| 8,691,547 B2 | 4/2014 | Omura et al. | |
| 2003/0082595 A1 | 5/2003 | Jiang et al. | |
| 2006/0063217 A1 | 3/2006 | Omura et al. | |
| 2007/0105173 A1 | 5/2007 | Takeshima et al. | |
| 2008/0014612 A1 | 1/2008 | Tsuji et al. | |
| 2009/0181408 A1 | 7/2009 | Tanaka et al. | |

FOREIGN PATENT DOCUMENTS

| | | |
|---|---|---|
| EP | 0 094 161 | 11/1983 |
| EP | 0 992 589 A2 | 4/2000 |
| EP | 1 584 675 A1 | 10/2005 |
| JP | 59-25700 | 2/1984 |
| JP | 10-239273 | 9/1998 |
| JP | 10-243786 | 9/1998 |
| JP | 2000-312588 A | 11/2000 |
| JP | 2000-350588 A | 12/2000 |
| JP | 2000-354495 A | 12/2000 |
| JP | 2001-037483 A | 2/2001 |
| JP | 2001-046078 | 2/2001 |
| JP | 2001-197888 A | 7/2001 |
| JP | 2001-346587 A | 12/2001 |
| JP | 2002-223772 A | 8/2002 |
| JP | 2002-526759 A | 8/2002 |
| JP | 2004-512047 A | 4/2004 |
| JP | 2004-173538 A | 6/2004 |

(Continued)

OTHER PUBLICATIONS

Tchan-Gi Bak; "Studies on Glucose Dehydrogenase of *Aspergillus oryzae*. II. Purification and Physical and Chemical Properties"; Biochemica Et Biophysica Acta; vol. 139; (1967); pp. 277-293.

(Continued)

*Primary Examiner* — Christian Fronda
(74) *Attorney, Agent, or Firm* — Finnegan, Henderson, Farabow, Garrett & Dunner, LLP

(57) ABSTRACT

Disclosed herein are a gene (polynucleotide) encoding an FAD-conjugated glucose dehydrogenase which can be characterized by reactivity to glucose, thermal stability, substrate-recognition performance, and low activity for maltose; a process for the production of the enzyme using a transformant cell transfected with the gene; a method for the determination of glucose; a reagent composition for use in the determination of glucose; and a biosensor for use in the determination of glucose. An embodiment is a polynucleotide encoding an FAD-conjugated glucose dehydrogenase, comprising a polypeptide whose amino acid sequence comprises X1-X2-X3-X4-X5-X6, wherein X1 and X2 independently represent an aliphatic amino acid residue; X3 and X6 independently represent a branched amino acid residue; and X4 and X5 independently represent a heterocyclic amino acid residue or an aromatic amino acid residue.

10 Claims, 2 Drawing Sheets

(56) References Cited

FOREIGN PATENT DOCUMENTS

| | | |
|---|---|---|
| JP | 2004-313172 A | 11/2004 |
| JP | 2004-313180 A | 11/2004 |
| JP | 2004-329143 | 11/2004 |
| JP | 2004-344145 A | 12/2004 |
| JP | 2008-154572 | 7/2008 |
| JP | 2008-206433 A | 9/2008 |
| WO | WO 98/20136 A1 | 5/1998 |
| WO | WO 02/072839 A1 | 9/2002 |
| WO | WO 03/012071 A2 | 2/2003 |
| WO | 2004/058958 | 7/2004 |
| WO | 2006/101239 | 9/2006 |

OTHER PUBLICATIONS

Osamu Yamada et al.; "Transformation System for *Aspergillus oryzae* with Double Auxotrophic Mutations, niaD and sC"; Biosci. Biotech. Biochem.; vol. 61, No. 8; (1997); pp. 1367-1369.

Osamu Yamada et al.; "dffA Gene from *Aspergillus oryzae* Encodes L-Ornithine N5-Oxygenase and is Indispensable for Defferiferrichrysin Biosynthesis"; Journal of Biosciences and Bioengineering; vol. 95, No. 1; (2003); pp. 82-88.

Tchan-Gi Bak; "Studies on Glucose Dehydrogenase of *Asperillus oryzae*. III. General Enzymatic Properties," Biochemica et Biophysica Acta.; vol. 146; (1967); pp. 317-327.

Tchan-Gi Bak; "Studies on Glucose Dehydrogenase of *Asperillus oryzae*. IV. Histidyl Residue as an Active Site"; Biochemica et Biophysica Acta.; vol. 146; (1967); pp. 328-335.

Roberto A. Chica et al.; "Semi-Rational Approaches to Engineering Enzyme Activity: Combining the Benefits of Directed Evolution and Rational Design"; Current Opinion in Biotechnology; vol. 16; (2005); pp. 378-384.

S. Sen et al.; "Developments in Directed Evolution for Improving Enzyme Functions"; Appl. Biochem. Biotechnol.; vol. 143; (2007); pp. 212-223.

Alignment to US Patent 7,553,649 SEQ ID No. 5; Sep. 2012.

Alignment to US Patent 7,553,649; SEQ ID No. 4; Jul. 2012.

Cavener, D. et al., "Biphasic expression and function of glucose dehydrogenase in *Drosophila melenogester*," Proc. Natl. Acad. Sci., 80: 6286-6288 (1983).

Harper's Review of Biochemistry, 20$^{th}$ ed., by Martin et al., 1985, p. 503.

Hayano, K. et al., "Purification and Properties of 3-Ketosucroseforming Enzyme from the Cells of *Agrobacterium tamefaciens*," The Journal of Biological Chemistry, 242(16): 3665-3672 (1967).

Inose, K. et al.; "Cloning and expression of the gene encoding catalytic subunit of thermostable glucose dehydrogenase from *Burkholderia cepacia* in *Escherichia coli*," Biochimica et Bioohysica Acta, 1645(2): 133-138 (2003).

Ishida et al. (ed.), "Laboratory Manual for Gene Expression, Production of useful protein in high expression system," Kodansha Scientific Ltd., (Partial English translations) pp. 100-129 (1994).

Iwashita, K. et al.; "Purification and Characterization of Extracellular and Cell Wall Bound β-Glucosidases from *Aspergillus kawachii*," Biosci. Biotechnol. Biochem., 62(10): 1938-1946 (1998).

Kataoka et al., "*Escherichia coli* transformant expressing the glucose dehydrogenase gene from *Bacillus megaterium* as a cofactor regenerator in a chiral alcohol production system," Biosci. Biotechnol. Biochem., 62: 167-169 (1998).

Kojima, S. et al., "Fundamental study for an oxygen-insensitive amperometric glucose sensor using a novel glucose dehydrogenase," Chemical Sensors, 20(Supplement B) 11: 768-769 (2004).

Kojima, N. et al.; "Shinki Glucose Dehydrogenase o Mochiita Sanso Fukan' no-sei Ketto Sensor no Kiso Kento (1)," The Japan Society for Analytical Chemistry Nenkai Koen Yoshishu, 53(18): 80 (2004).

Machida et al., "Genome sequencing and analysis of *Aspergillus oryzae*," Nature, 438: 1157-1161 (2005).

Morrison et al.; "Characterization of a glucose 3-dehydrogenase from the cultivated mushroom (*Agaricus bisporus*)," Appl. Microbial. Biotechnol., 51: 58-64 (1999).

New Biochemical Experiment Course 1 Protein II "Primary Structure", Tokyo Kagaku Dojin, 1$^{st}$ edition, 2$^{nd}$ printing, pp. 1-24 (Dec. 1, 1993).

Pharmaceutical and Food Safety Bureau Issue No. 0207005, Safety Measures of Simple Instrument for Self-Checking Blood Glucose and Glucose Kit for Self-Testing Blood Glucose (Using Pyrrolo-Quinoline Quinone as Coenzyme in Glucose Dehydrogenase Method), Feb. 7, 2005.

Rolke et al., "Functional analysis of $H_2O_2$-generating systems in *Botrytis cinerea*: the major Cu—Zn-superoxide dismutase (BC5OD1) contributes to virulence on French bean, whereas a glucose oxidase (BCGOD1) is dispensable," Molecular Plant Pathology, 5(1): 17-27 (2004).

Yoshino et al., "Cloning and expression of catalytic subunit of glucose dehydrogenase from *Burkholderia cepacia*," Society for Biotechnology, Japan (Oct. 28-30, 2002).

Sode, K. et al., "A novel thermostable glucose dehydrogenase varying temperature properties by altering its quaternary structures," Enzyme and Microbial Technology, 19: 82-85 (1996).

Summary of the Annual Meeting of Japan Society for Bioscience 2004, "Fundamental Review for Non-Oxygen Sensitive Glucose Sensor Using Novel Glucose Dehydrogenase," Biotechnology and Agrochemistry, 96, 2A25p11 (Mar. 5, 2004). (Author not indicated).

Tsugawa, W. et al., "Purification of a Marine Bacterial Glucose Dehydrogenase from *Cytophaga marinotlava* and its Application for Measurement of 1,5-Anhydro-D-Glucitol," Applied Biochemistry and Biotechnology, 56: 301-310 (1996).

Tsugawa, W. et al., "Fluorescent measurement of 1,5-anhydro-D-glucitol based on a novel marine bacterial glucose dehydrogenase," Enzyme and Microbial Technology, 22: 269-274 (1998).

Tswimura, S. et al., "Absolute quantification of glucose by coulometry in novel glucose dehydrogenase," Abstract of the 72$^{nd}$ Meeting of the Electrochemical Society of Japan, 2D04 (2005).

Tsujimura, S. et al., "Novel FAD-Dependent Glucose Dehydrogenase for a Dioxygen-Insensitive Glucose Biosensor," Biosci. Biotechnol. Biochem., 70(3): 654-659 (2006).

UniProt Accession No. G8E4B4, Glucose dehydrogenase, created Jan. 25, 2012.

Vole, J. et al., "Pyranose 2-dehydrogenase, a novel sugar oxidoreductase from the basidiomycete fungus *Agaricus bisporus*," Arch Microbial, 167:119-125 (1997).

Vole, J. et al., "Screening of basidiomycete fungi for the quinone-dependent sugar C-2/C-3 oxidoreductase, pyranose dehydrogenase, and properties of the enzyme from *Macrolepiota rhacodes*," Arch Microbial, 176: 178-186 (2001).

Witt, S. et al., "Structural and Kinetic Properties of Nonglycosylated Recombinant *Penicillium amagasakiense* Glucose Oxidase Expressed in *Escherichia coli*," Applied and Environmental Microbiology, 64(4): 1405-1411 (1998).

Yoshida, H. et al., "Construction of multi-chimeric pyrroloquinoline quinone glucose dehydrogenase with improved enzymatic properties and application in glucose monitoring," Biotechnology Letters, 22(18):1505-1510 (2000).

Yurimoto et al., "Heterologous gene expression system by methanol-utilizing yeast," Chemistry & Biology, 38(8):533-540 (2000). (Partial English translations).

Notice of Submission of Published Documents dated Feb. 10, 2009 for counterpart Japanese Patent Application No. 2007-509374.

Office Action issued on Aug. 2, 2011 in connection with corresponding to Japanese Patent Application No. JP 2007-509374, English language translation attached.

Communication pursuant to Rule 114(2) EPC issued Aug. 26, 2010 by the European Patent Office in connection with European Patent Application No. 06730146.5.

European Search Report issued for corresponding application No. EP 11156659.2, dated Jun. 28, 2011.

European Search Report issued for corresponding application No. EP 11156661.8, dated Jun. 6, 2011.

European Search Report issued for corresponding application No. EP 11156657.6, dated Aug. 25, 2011.

European Search Report issued for corresponding application No. EP 11156649.3, dated Sep. 23, 2011.

(56) References Cited

OTHER PUBLICATIONS

European Search Report issued for corresponding application No. EP 11156664.2, dated Sep. 23, 2011.
International Search Report issued for International Application No. PCT/JP2006/306198 mailed Apr. 25, 2006.
Office Action mailed Jul. 25, 2012, in U.S. Appl. No. 12/866,071.
Amendment and Response to Restriction Requirement filed Aug. 27, 2012, in U.S. Appl. No. 12/866,071.
Office Action mailed Sep. 25, 2012, in U.S. Appl. No. 12/866,071.
Amendment filed Dec. 26, 2012, in U.S. Appl. No. 12/866,071.
Final Office Action mailed Jan. 31, 2013, in U.S. Appl. No. 12/866,071.
Amendment after Final filed Mar. 13, 2013, in U.S. Appl. No. 12/866,071.
Office Action mailed Apr. 9, 2012, in U.S. Appl. No. 11/886,885.
Amendment and Response to Reply Requirement filed Jul. 6, 2012, in U.S. Appl. No. 11/886,885.
Office Action mailed Sep. 13, 2012, in U.S. Appl. No. 11/886,885.
Reply to Office Action under 37 C.F.R. § 1.111 filed Dec. 11, 2012, in U.S. Appl. No. 11/886,885.
Final Office Action mailed Feb. 13, 2013, in U.S. Appl. No. 11/886,885.
Amendment and Reply to Final Office Action under 37 C.F.R. § 1.116 Apr. 12, 2013, in U.S. Appl. No. 11/886,885.
Advisory Action mailed May 8, 2013, in U.S. Appl. No. 11/886,885.
Interview Summary mailed Oct. 15, 2013, in U.S. Appl. No. 11/886,885.
Notice of Allowance and Fee(s) Due mailed Nov. 21, 2013, in U.S. Appl. No. 11/886,885.

FAD-CONJUGATED GLUCOSE DEHYDROGENASE GENE

TECHNICAL FIELD

The present invention relates to a novel gene (polynucleotide) encoding a flavin adenine dinucleotide (FAD) conjugated glucose dehydrogenase; a process for the production of the enzyme using a transformant cell transfected with the gene; a recombinant FAD-conjugated glucose dehydrogenase; and a method for the determination of glucose, a reagent composition for use in the determination of glucose, a biosensor for use in the determination of glucose and others, each characterized by using the enzyme.

BACKGROUND ART

The blood glucose level is an important marker for diabetes. As for an examination for diabetes, other than a clinical examination performed in a hospital laboratory or the like, a simple determination (point-of-care testing (POCT)) such as a simple examination by a medical staff member or the like or a self-examination by a patient himself or herself is performed.

This simple determination is performed using a glucose diagnostic kit or a determination device (POCT device) such as a biosensor, and in such a POCT device, conventionally a glucose oxidase has been used. However, such a glucose oxidase is affected by a dissolved oxygen concentration and an error in the measured value is caused. Therefore, it is recommended to use of a glucose dehydrogenase which is not affected by oxygen.

Examples of the glucose dehydrogenase include a coenzyme-unconjugated glucose dehydrogenase which requires nicotinamide adenine dinucleotide (NAD) or nicotinamide adenine dinucleotide phosphate (NADP) as a coenzyme and a coenzyme-conjugated glucose dehydrogenase which requires pyrroloquinoline quinone (PQQ), flavin adenine dinucleotide (FAD) or the like as a coenzyme. Among these, the coenzyme-conjugated glucose dehydrogenase has advantages that the enzyme is less likely to be affected by impurities as compared with the coenzyme-unconjugated glucose dehydrogenase, the determination sensitivity is high, and further, in principle, the POCT device can be produced at low cost.

However, a conventional PQQ-conjugated glucose dehydrogenase has low stability and also has a disadvantage that it reacts also with maltose and galactose. Maltose is a sugar used in an infusion, and when the PQQ-conjugated glucose dehydrogenase reacts with maltose, a blood glucose POCT device displays a higher blood glucose level than the actual value. Due to this, a patient administers an unnecessary insulin injection to the patient himself or herself, resulting in the occurrence of a hypoglycemic event such as impaired consciousness or comatose states, which has been a big problem.

In particular, as for the current use of the blood glucose POCT device, not only it is used for simply determining the blood glucose, but importance as a means for self-care and self-treatment by a patient is increasing and the use of a self-monitoring of blood glucose (SMBG) device to be used for the purpose at home is expanding. Therefore, the demand for determination accuracy is considered to be very high.

In fact, an official notice to draw attention about the use of a blood glucose meter using an enzyme requiring PQQ as a coenzyme was issued from the Ministry of Health, Labour and Welfare in Japan in February 2005 to patients under administration of maltose infusion or dialysate containing icodextrin (Pharmaceutical and Food Safety Bureau Notice No. 0207005 issued on Feb. 7, 2005, etc.).

On the other hand, as the coenzyme-conjugated glucose dehydrogenase which catalyzes the dehydrogenation reaction of glucose and requires FAD as a coenzyme, an *Agrobacterium tumefaciens*-derived enzyme (J. Biol. Chem. (1967) 242: 3665-3672), a *Cytophaga marinoflava*-derived enzyme (Appl. Biochem. Biotechnol. (1996) 56: 301-310), a *Halomonas* sp. α-15-derived enzyme (Enzyme Microb. Technol. (1998) 22: 269-274), an *Agaricus bisporus*-derived enzyme (Arch. Microbiol. (1997) 167: 119-125, Appl. Microbiol. Biotechnol. (1999) 51: 58-64), and a *Macrolepiota rhacodes*-derived enzyme (Arch. Microbiol. (2001) 176: 178-186) have been reported. However, these enzymes oxidize a hydroxy group at the 2- and/or 3-position of glucose, have a high activity for maltose, and have a low selectivity for glucose. Further, a coenzyme-conjugated glucose dehydrogenase derived from *Burkholderia cepacia* having a high activity for maltose in the same manner is also known. However, an original naturally occurring enzyme is a heterooligomer enzyme comprising three kinds of subunits: α, β, and γ, and is known as a membrane-bound enzyme. Therefore, there are problems that a lysis treatment is required for obtaining this enzyme, simultaneous cloning of a necessary subunit is required for exhibiting a sufficient activity by cloning, and so on.

On the other hand, the present inventors have purified a novel soluble coenzyme-conjugated glucose dehydrogenase which requires FAD as a coenzyme and is not a membrane-bound type from *Aspergillus terreus* (Patent document 1). This coenzyme-conjugated glucose dehydrogenase described in Patent document 1 has unprecedented excellent properties that it oxidizes a hydroxy group at the 1-position of glucose, has excellent substrate (glucose) recognition performance, is not affected by dissolved oxygen, and also has a low activity for maltose (the activity for maltose is 5% or less and the activity for galactose is also 5% or less with the activity for glucose taken as 100%).

However, the coenzyme-conjugated glucose dehydrogenase described in Patent document 1 is isolated and extracted from a liquid culture of a wild-type microorganism (such as a microorganism belonging to the genus *Aspergillus*), and the production amount thereof is limited. Besides the fact that the production amount of the enzyme is extremely small, a large amount of sugars are linked to the enzyme, and the enzyme is in the form covered with sugars which are different from N-linked or O-linked sugar chains bound to a common enzyme (which might be called "a sugar-embedded enzyme"). Therefore, the activity of the enzyme is difficult to detect (the enzymatic activity is low), the sugar chains cannot be enzymatically or chemically removed, and as a result, in electrophoresis, almost no staining is achieved by common protein staining (coomassie brilliant blue G-250 or the like), and also it is difficult to read amino terminal and internal amino acid sequences of the enzyme which provide information necessary for acquiring a gene from the enzyme subjected to a common purification procedure. Accordingly, it is not publicly known that the cloning of a gene of this enzyme was successful or the expression of the activity of this enzyme was confirmed.

On the other hand, the existence of a coenzyme-conjugated glucose dehydrogenase derived from *Aspergillus oryzae* was suggested in 1967 (Non-patent document 1). However, only partial enzymatic properties were revealed, and although a property that the enzyme does not act on maltose was suggested, there has been no detailed report with respect to the coenzyme-conjugated glucose dehydrogenase derived from

*Aspergillus oryzae* since then, and also there has been no subsequent report with respect to a coenzyme-conjugated glucose dehydrogenase derived from other microorganisms or an enzyme which oxidizes a hydroxy group at the 1-position of glucose, and also no report with respect to the amino acid sequence or gene of the coenzyme-conjugated glucose dehydrogenase has been found at all.

Further, an idea of using a glucose dehydrogenase EC 1.1.99.10 in glucose determination (see Patent document 2) is known, however, an FAD-conjugated glucose dehydrogenase has not been produced at a practical level, and the enzyme has not been actually used in a sensor or put into a practical use. The reason is considered that the activity of this enzyme in microbial cells was very low, and even if the enzyme was secreted to the outside of microbial cells, the amount thereof was very small, and moreover, the enzyme was covered with a large amount of sugars, and therefore the activity was low, and even the detection thereof was difficult, and thus the gene thereof could not be cloned.

Patent document 1: WO 2004/058958
Patent document 2: JP-A-59-25700
Non-patent document 1: Biochem. Biophys. Acta., 139, 277-293, 1967

DISCLOSURE OF THE INVENTION

Problems that the Invention is to Solve

As genetic engineering methods for modifying a PQQ-conjugated glucose dehydrogenase, a lot of techniques have already been known, and these conventional techniques mainly provide a modified PQQ-conjugated glucose dehydrogenase for improving disadvantages of the conventional PQQ-conjugated glucose dehydrogenase such as low substrate specificity and low stability of the enzyme and a modified genetic material for producing the modified PQQ-conjugated glucose dehydrogenase by genetic engineering.

However, in the case of the modified PQQ-conjugated glucose dehydrogenase produced using the modified genetic material, the activity for maltose is still more than about 10% with the activity for glucose taken as 100%, or as a result of decreasing the reactivity to maltose, also the primary reactivity (specific activity) to glucose is decreased. Therefore, the function as a glucose sensor is not sufficient from the viewpoint of the activity determined by an electrochemical determination method using a sufficient amount of a substrate, and the current situation is that the enzyme cannot be used in a POCT device or the like. In addition, the coenzyme PQQ required for the expression of the activity of the PQQ-conjugated glucose dehydrogenase has a problem that it cannot be produced in *Escherichia coli* which is widely and generally used as a recombinant host and it is necessary to produce a recombinant by limiting it to a host microorganism that produces PQQ (Pseudomonas or the like).

Accordingly, an object of the invention is to solve the above problems and to provide a novel gene (polynucleotide) encoding an FAD-conjugated glucose dehydrogenase having excellent properties that it has excellent reactivity to glucose, excellent thermal stability, and excellent substrate-recognition performance and also has a low activity for maltose; a process for the production of the enzyme using a transformant cell transfected with the gene; and a method for the determination of glucose, a reagent composition for use in the determination of glucose, a biosensor for use in the determination of glucose and others, each characterized by using the obtained enzyme.

Means for Solving the Problems

The present inventors made intensive studies in order to achieve the above object, and as a result, they found that in order to significantly express an FAD-conjugated glucose dehydrogenase in an *Aspergillus oryzae* strain, it was necessary that an amino acid sequence (AGVPWV) be contained in a polypeptide encoding a gene of the enzyme, and also confirmed that the activity was substantially lost when at least one amino acid residue in the amino acid sequence was deleted, and thus, the invention was completed. That is, the invention relates to the following aspects.

[Aspect 1] A polynucleotide encoding an FAD-conjugated glucose dehydrogenase, comprising a polypeptide containing an amino acid sequence: X1-X2-X3-X4-X5-X6 (wherein X1 and X2 independently represent an aliphatic amino acid residue; X3 and X6 independently represent a branched amino acid residue; and X4 and X5 independently represent a heterocyclic amino acid residue or an aromatic amino acid residue).

[Aspect 2] A polynucleotide encoding a polypeptide (a), (b) or (c) defined below:
(a) a polypeptide which comprises an amino acid sequence represented by SEQ ID NO: 1;
(b) a polypeptide which comprises an amino acid sequence having substitution, deletion, or addition of one to several amino acid residues in the amino acid sequence of the amino acid sequence (a) and has an FAD-conjugated glucose dehydrogenase activity; or
(c) a polypeptide which comprises an amino acid sequence having a homology of 70% or more to the amino acid sequence (a) and has an FAD-conjugated glucose dehydrogenase activity.

[Aspect 3] A polynucleotide (d), (e) or (f) defined below:
(d) a polynucleotide which comprises a base sequence represented by SEQ ID NO: 2 or 3;
(e) a polynucleotide which hybridizes to a polynucleotide comprising a base sequence complementary to a polynucleotide comprising a base sequence (d) under stringent conditions and encodes a polypeptide having an FAD-conjugated glucose dehydrogenase activity; or
(f) a polynucleotide which comprises a base sequence having a homology of 70% or more to the polynucleotide comprising a base sequence (d) and encodes a polypeptide having an FAD-conjugated glucose dehydrogenase activity.

[Aspect 4] A polynucleotide which has a DNA fragment amplifiable by PCR using a combination of a sense primer comprising a base sequence encoding the amino acid sequence: AGVPWV with a reverse primer comprising a base sequence on the 3'-terminal side of a polynucleotide encoding an FAD-conjugated glucose dehydrogenase derived from *Aspergillus oryzae* or a combination of an antisense primer for a base sequence encoding the amino acid sequence: AGVPWV with a forward primer comprising a base sequence on the 5'-terminal side of a polynucleotide encoding an FAD-conjugated glucose dehydrogenase derived from *Aspergillus oryzae*, and encodes a polypeptide having an FAD-conjugated glucose dehydrogenase activity.

[Aspect 5] A polynucleotide which hybridizes to a probe comprising a base sequence encoding the amino acid sequence: AGVPWV under stringent conditions and encodes a polypeptide having an FAD-conjugated glucose dehydrogenase activity.

[Aspect 6] A polynucleotide encoding an FAD-conjugated glucose dehydrogenase derived from *Aspergillus oryzae*, characterized by showing a value of enzymatic activity for maltose of 10% or less and a value of enzymatic activity for D-galactose of 5% or less with a value of enzymatic activity for D-glucose taken as 100%.

[Aspect 7] A polynucleotide encoding an FAD-conjugated glucose dehydrogenase derived from *Aspergillus oryzae*, characterized by having an enzymatic activity of 300 U/mg or more.

[Aspect 8] A recombinant vector containing the above polynucleotide.

[Aspect 9] A transformant cell produced using the above recombinant vector.

[Aspect 10] A process for the production of an FAD-conjugated glucose dehydrogenase, characterized by culturing the above transformant cell, and collecting an FAD-conjugated glucose dehydrogenase having an activity to dehydrogenate glucose from the resulting culture.

[Aspect 11] A recombinant FAD-conjugated glucose dehydrogenase encoded by the above polynucleotide.

[Aspect 12] A method for the determination of glucose, characterized by using the above FAD-conjugated glucose dehydrogenase.

[Aspect 13] A reagent composition for use in the determination of glucose, characterized by comprising the above FAD-conjugated glucose dehydrogenase.

[Aspect 14] A biosensor for use in the determination of glucose, characterized by using the above FAD-conjugated glucose dehydrogenase.

Advantage of the Invention

By using the polynucleotide of the invention, an FAD-conjugated glucose dehydrogenase having excellent properties that it has excellent substrate (glucose) recognition performance and also has a low activity for maltose can be produced uniformly in a large amount by, for example, a recombinant DNA technique.

Further, in the thus produced enzyme, the sugar amount which is a problem of the FAD-conjugated glucose dehydrogenase can be controlled according to the purpose, and therefore, by preparing the enzyme in which the sugar content has been reduced, in the determination of blood glucose or the like, it is also possible to alter the activity for sugars (such as glucose) in a sample.

BEST MODE FOR CARRYING OUT THE INVENTION

Figure 1:
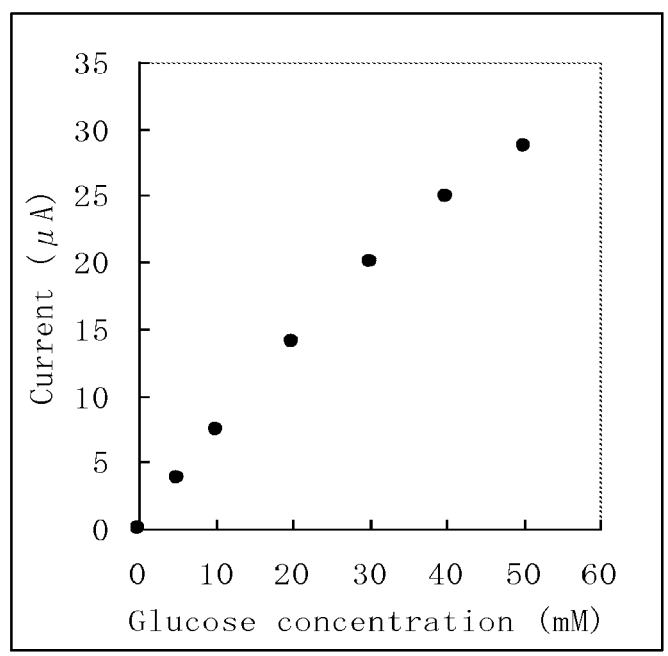
FIG. 1 shows a calibration curve of glucose concentration using an enzyme-immobilized electrode.

It is one of the technically important points that an amino acid sequence: X1-X2-X3-X4-X5-X6 (wherein X1 and X2 represent the same or a different aliphatic amino acid residue; X3 and X6 represent the same or a different branched amino acid residue; and X4 and X5 represent the same or a different heterocyclic amino acid residue or aromatic amino acid residue), in other words, a polypeptide comprising 6 amino acid residues is contained in the FAD-conjugated glucose dehydrogenase of the invention. According to this configuration, the enzyme is significantly expressed in microbial cells. Incidentally, the expressed enzyme is not necessarily secreted to the outside of microbial cells, and remains in microbial cells in some cases. In contrast, as specifically shown in Examples of this description, even if a gene encodes an enzyme considered to be an FAD-conjugated glucose dehydrogenase based on the homology of the entire amino acid sequence or the like, when the gene does not encode the polypeptide comprising the amino acid sequence, it does not express a protein having an FAD-conjugated glucose dehydrogenase activity.

The above-mentioned amino acid sequence comprising 6 amino acid residues is preferably located at positions 202 to 207 of a polypeptide which is an FAD-conjugated glucose dehydrogenase, or at least one of X1 to X6 is as follows: X1 is alanine (A), X2 is glycine (G), X3 is valine (V), X4 is proline (P), X5 is tryptophan (W), or X6 is valine (V). For example, as a preferred example, the amino acid sequence: AGVPWV (SEQ ID NO: 4) can be exemplified.

In the invention, the "FAD-conjugated glucose dehydrogenase" refers to a soluble protein which catalyzes a reaction of the dehydrogenation (oxidation) of a hydroxy group at the 1-position of glucose in the presence of an electron acceptor and has an activity for maltose relative to the activity for glucose of 10% or less, and the enzyme is characterized by the following properties.

1) Flavin adenine dinucleotide (FAD) is required as a coenzyme.
2) Oxygen is not used as an electron acceptor.
3) The activity for maltose relative to the activity for glucose is 10% or less.

Among the FAD-conjugated glucose dehydrogenases of the invention, as the enzyme having the amino acid sequence: AGVPWV, particularly, one derived from *Aspergillus oryzae* is preferred. Typical examples of a strain thereof include NBRC 5375 strain, NBRC 4079 strain, NBRC 4203 strain, NBRC 4214 strain, NBRC 4268 strain, NBRC 5238 strain, NBRC 6215 strain, NBRC 30104 strain, and NERC 30113 strain as shown in the following Table 1. The amino acid sequence: AGVPWV is contained in the amino acid sequence of the enzyme in the vicinity of positions 202 to 207 (derived from NBRC 5375 strain) (in the case of an enzyme derived from other strain, positions corresponding to the positions) with the initiator amino acid residue M in a signal sequence region counted as position 1.

For example, the amino acid sequence of the FAD-conjugated glucose dehydrogenase expressed by *Aspergillus oryzae* NBRC 5375 strain is represented by SEQ ID NO: 1 (containing a signal peptide), the base sequence of a chromosomal DNA encoding the same is represented by SEQ ID NO: 2, and a cDNA corresponding to the amino acid residues represented by SEQ ID NO: 1 is represented by SEQ ID NO: 3. Incidentally, in SEQ ID NO: 2 or 3, the base sequence encoding the amino acid sequence: AGVPWV is GCTGGT-GTTCCATGGGTT (SEQ ID NO: 5).

Accordingly, the polynucleotide of the invention includes, in addition to those derived from *Aspergillus oryzae* strains described above, a polynucleotide encoding a polypeptide (a), (b) or (c) defined below:

(a) a polypeptide which comprises an amino acid sequence represented by SEQ ID NO: 1;
(b) a polypeptide which comprises an amino acid sequence having substitution, deletion, or addition of one to several amino acid residues in the amino acid sequence (a) and has an FAD-conjugated glucose dehydrogenase activity; or (c) a polypeptide which comprises an amino acid sequence having a homology of 70% or more to the amino acid sequence (a) and has an FAD-conjugated glucose dehydrogenase activity.

Further, the polynucleotide of the invention includes a polynucleotide (d), (e) or (f) defined below:

(d) a polynucleotide which comprises a base sequence represented by SEQ ID NO: 2 or 3;

(e) a polynucleotide which hybridizes to a polynucleotide comprising a base sequence complementary to a polynucleotide comprising a base sequence (d) under stringent conditions and encodes a polypeptide having an FAD-conjugated glucose dehydrogenase activity; or (f) a polynucleotide which comprises a base sequence having a homology of 70% or more to the polynucleotide comprising a base sequence (d) and encodes a polypeptide having an FAD-conjugated glucose dehydrogenase activity.

In particular, it is preferred that the above polypeptide (b) or (c) contains the amino acid sequence: X1-X2-X3-X4-X5-X6, or the polynucleotide (e) or (f) contains a base sequence encoding the amino acid sequence. Further, it is preferred that this amino acid sequence is AGVPWV.

In this description, the amino acid sequence or base sequence having a homology of 70% or more refers to a sequence showing a homology of at least 70%, preferably 75% or more, more preferably 80% or more, further more preferably 90% or more, particularly preferably 95% or more to the full-length of a standard sequence to be compared, respectively. The homology percentage of such a sequence can be calculated using a disclosed or commercially available software with an algorithm that makes a comparison using the standard sequence as a reference sequence. For example, BLAST, FASTA, or GENETYX (manufactured by Software Development Co., Ltd.), or the like can be used. These can be used with default parameters.

In the invention, as specific conditions for the "hybridization under stringent conditions" when polynucleotides are hybridized, for example, incubation at 42° C. in 50% formamide, 5×SSC (150 mM sodium chloride, 15 mM trisodium citrate, 10 mM sodium phosphate, 1 mM ethylenediaminetetraacetic acid, pH 7.2), 5×Denhardt's solution, 0.1% SDS, 10% dextran sulfate, and 100 μg/mL modified salmon sperm DNA, followed by washing of the filter at 42° C. in 0.2×SSC can be exemplified.

Further, the polynucleotide of the invention includes a polynucleotide which has a DNA fragment amplifiable by PCR using a combination of a sense primer comprising a base sequence encoding the amino acid sequence: AGVPWV with a reverse primer comprising a base sequence on the 3'-terminal side of a polynucleotide encoding an FAD-conjugated glucose dehydrogenase derived from *Aspergillus oryzae* or a combination of an antisense primer for a base sequence encoding the amino acid sequence: AGVPWV with a forward primer comprising a base sequence on the 5'-terminal side of a polynucleotide encoding an FAD-conjugated glucose dehydrogenase derived from *Aspergillus oryzae*, and encodes a polypeptide having an FAD-conjugated glucose dehydrogenase activity.

Alternatively, the polynucleotide of the invention includes a polynucleotide which hybridizes to a probe comprising a base sequence encoding the amino acid sequence: AGVPWV under stringent conditions and encodes a polypeptide having an FAD-conjugated glucose dehydrogenase activity.

The base sequence encoding the amino acid sequence: AGVPWV is preferably GCTGGTGTTCCATGGGTT. Further, the respective conditions for the above-mentioned PCR and hybridization under stringent conditions can be suitably selected by those skilled in the art in accordance with the description of Examples in this description.

Further, the polynucleotide of the invention includes a polynucleotide encoding an FAD-conjugated glucose dehydrogenase, which shows a value of enzymatic activity for maltose of 10% or less, preferably 5% or less, more preferably 3% or less, and a value of enzymatic activity for D-galactose of 5% or less, preferably 3% or less, more preferably 2% or less, further more preferably 1% or less with a value of enzymatic activity for D-glucose taken as 100%; or a polynucleotide encoding an FAD-conjugated glucose dehydrogenase having an enzymatic activity of a specific activity per protein of 300 U/mg or more, preferably 500 U/mg or more, more preferably 1,000 U/mg or more. Incidentally, the "specific activity per protein" as used herein is, for example, a measurement determined in a state confirmed as a single band by SDS-PAGE of a concentrated culture supernatant as described in Example 7 of this description.

Incidentally, in the invention, the "polynucleotide" refers to a molecule having 100 or more phosphate esters of nucleosides in which a purine or a pyrimidine is attached to a sugar via a β-N-glycosidic bond (ATP (adenosine triphosphate), GTP (guanosine triphosphate), CTP (cytidine triphosphate), or UTP (uridine triphosphate); or dATP (deoxyadenosine triphosphate), dGTP (deoxyguanosine triphosphate), dCTP (deoxycytidine triphosphate), or dTTP (deoxythymidine triphosphate). Specific examples thereof include a chromosomal DNA encoding an FAD-conjugated glucose dehydrogenase, a mRNA transcribed from the chromosomal DNA, a cDNA synthesized from the mRNA, and a polynucleotide amplified by PCR using any of these as a template. An "oligonucleotide" refers to a molecule in which 2 to 99 nucleotides are linked to one another. Further, the "polypeptide" refers to a molecule formed from 30 or more amino acid residues which are linked to one another through an amide bond (peptide bond) or an unnatural residual linkage, and also those with the addition of a sugar chain, those with the artificial chemical modification, and the like are included.

The most specific mode of the polynucleotide (gene) of the invention is a polynucleotide containing the base sequence represented by SEQ ID NO: 2 or 3. The polynucleotide which is a chromosomal DNA typified by SEQ ID NO: 2 can be obtained by, for example, preparing a chromosomal DNA library from *Aspergillus oryzae* NBRC 5375 strain, and screening the chromosomal DNA library by a method known to those skilled in the art using a plurality of oligonucleotide probes prepared based on amino acid sequences obtained by determining amino acid residues of N-terminal and internal sequences of an FAD-conjugated glucose dehydrogenase derived from *Aspergillus terreus* described in Patent document 1 by the Edman sequencing method or the like, and the genome sequence information of *Aspergillus oryzae* (NBRC 100959 strain) disclosed in DOGAN (Database of the Genomes Analyzed at NITE) (website http://www.bio.nite.go.jp/dogan/Top) in January, 2006 as a result of the "*Aspergillus oryzae* genome analysis project".

The labeling of the probe can be performed by an arbitrary method known to those skilled in the art such as a radioisotope (RI) method or a non-RI method, however, a non-RI method is preferably used. Examples of the non-RI method include a fluorescence labeling method, a biotinylation method, and a chemiluminescence method, however, a fluorescence labeling method is preferably used. As a fluorescent substance, those capable of binding to a base moiety of an oligonucleotide is suitably selected and can be used, and specifically, a cyanine dye (such as Cy3 or Cy5 in Cy Dye™ series), a rhodamine 6G reagent, N-acetoxy-N2-acetylaminofluorene (AAF), AAIF (iodine derivative of AAF), or the like can be used.

Alternatively, the polynucleotide which is a cDNA typified by SEQ ID NO: 3 can be obtained by, for example, as specifically described in Examples of this specification, any of a variety of PCR methods known to those skilled in the art using the oligonucleotide primer (probe) set prepared in the above with a cDNA library as a template, or also by the RT-PCR method using the total RNA or mRNA extracted from *Aspergillus oryzae* NBRC 5375 strain as a template. Incidentally, in the case where a primer is designed, the size (the number of bases) of the primers is from 15 to 40 bases, preferably from 15 to 30 bases in consideration of achieving the specific annealing thereof to a template DNA. However, in the case where LA (long and accurate) PCR is performed, the size of at least 30 bases is effective. Complementary sequences between the both primers should be avoided so that a set of or a pair (2 strands) of primers comprising a sense strand (on the 5'-terminal side) and an antisense strand (on the 3'-terminal side) may not anneal to each other. Further, in order to secure stable binding to the template DNA, the GC content should be about 50% so that GC-rich or AT-rich regions should not be unevenly distributed within the primers. Since the annealing temperature depends on Tm (melting temperature), primers having a Tm value in the range from 55 to 65° C. and similar to each other are selected in order to obtain a highly specific PCR product. In addition, it is necessary to note that the final concentration of the primers used in PCR should be adjusted to about 0.1 to about 1 µM and the like. Further, a commercially available software for primer designing, for example, Oligo™ (manufactured by National Bioscience, Inc. (U.S.A.)), GENETYX (manufactured by Software Development Co., Ltd.), or the like can be also used.

Incidentally, such an oligonucleotide probe or an oligonucleotide primer set can also be prepared by cleaving the cDNA which is the polynucleotide of the invention with a suitable restriction enzyme.

Further, the polynucleotide of the invention can be prepared by modifying the above-mentioned cDNA of the FAD-conjugated glucose dehydrogenase derived from *Aspergillus oryzae* NBRC 5375 strain by a known mutation introduction method, a mutagenic PCR method, or the like. Further, the polynucleotide of the invention can be obtained from a chromosomal DNA of an *Aspergillus oryzae* strain other than NBRC 5375 strain or a cDNA library thereof by a probe hybridization method using an oligonucleotide prepared based on the nucleotide sequence information of SEQ ID NO: 1. The polynucleotide can be obtained by variously changing stringent conditions when performing hybridization. The stringent conditions are defined by a salt concentration, an organic solvent (such as formaldehyde) concentration, a temperature, and the like in the hybridization and washing steps, and for example, various conditions known to those skilled in the art as disclosed in the description of U.S. Pat. No. 6,100,037 or the like can be adopted.

Further, the polynucleotide of the invention can be synthesized in vitro by a well-known chemical synthesis technique as described in a document (such as Carruthers (1982) Cold Spring Harbor Symp. Quant. Biol. 47: 411-418; Adams (1983) J. Am. Chem. Soc. 105: 661; Belousov (1997) Nucleic Acid Res. 25: 3440-3444; Frenkel (1995) Free Radic. Biol. Med. 19: 373-380; Blommers (1994) Biochemistry 33: 7886-7896; Narang (1979) Meth. Enzymol. 68: 90; Brown (1979) Meth. Enzymol. 68: 109; Beaucage (1981) Tetra. Lett. 22: 1859; or U.S. Pat. No. 4,458,066).

The recombinant vector of the invention is a cloning vector or an expression vector, and an appropriate recombinant vector is used depending on the kind of a polynucleotide to be used as an insert, an intended use thereof, or the like. For example, in the case where an FAD-conjugated glucose dehydrogenase is produced using a cDNA or an ORF region thereof as an insert, an expression vector for in vitro transcription, or an expression vector suitable for the respective prokaryotic cells such as *Escherichia coli* and *Bacillus subtilis*; and eukaryotic cells such as yeasts, filamentous fungi (such as molds), insect cells, and mammalian cells can be used.

As the transformant cell of the invention, for example, a prokaryotic cell such as *Escherichia coli* or *Bacillus subtilis*; a eukaryotic cell such as a yeast, a mold, an insect cell, or a mammalian cell; or the like can be used. Such a transformant cell can be prepared by introducing a recombinant vector into a cell by a known method such as an electroporation method, a calcium phosphate method, a liposome method, or a DEAE dextran method. Specific examples of the recombinant vector and the transformant cell include a recombinant vector shown in the below-mentioned Examples and a transformed *Escherichia coli* and a transformed mold prepared with this vector.

In the case where the FAD-conjugated glucose dehydrogenase of the invention is produced by expressing a DNA in a microorganism such as *Escherichia coli*, a recombinant expression vector in which the above-mentioned polynucleotide is introduced into an expression vector having an origin, a promoter, a ribosome-binding site, a DNA cloning site, a terminator sequence, and the like and replicable in the microorganism is prepared, a host cell is transformed with this expression vector, and the resulting transformant is cultured, whereby the FAD-conjugated glucose dehydrogenase can be produced in a large amount in the microorganism. At this time, if a start codon and a stop codon are introduced upstream and downstream of an arbitrary coding region and the DNA is expressed, an FAD-conjugated glucose dehydrogenase fragment containing the arbitrary region can also be obtained. Alternatively, the enzyme can also be expressed as a fusion protein with another protein. By cleaving this fusion protein with a suitable protease, the target FAD-conjugated glucose dehydrogenase can also be obtained. Examples of the expression vector for *Escherichia coli* include a pUC system, pBluescript II, a pET expression system, a pGEX expression system, and a pCold expression system.

Alternatively, in the case where the FAD-conjugated glucose dehydrogenase is produced by expressing it in a eukaryotic cell, a recombinant vector is prepared by inserting the above-mentioned polynucleotide into an expression vector for a eukaryotic cell having a promoter, a splicing region, a poly(A) addition site, and the like, and the resulting recombinant vector is introduced into a eukaryotic cell, whereby the FAD-conjugated glucose dehydrogenase can be produced in the eukaryotic cell. The polynucleotide can be maintained in a cell in a state of a plasmid or the like, or can be maintained by incorporating the polynucleotide into a chromosome. Examples of the expression vector include pKA1, pCDM8, pSVK3, pSVL, pBK-CMV, pBK-RSV, an EBV vector, pRS, and pYE82. Further, if pIND/V5-His, pFLAG-CMV-2, pEGFP-N1, pEGFP-C1, or the like is used as the expression vector, an FAD-conjugated glucose dehydrogenase polypeptide can also be expressed as a fusion protein to which any of a variety of tags such as a His tag, a FLAG tag, or GFP has been attached. As the eukaryotic cell, a cultured mammalian cell such as a monkey kidney cell COS-7, or a Chinese hamster ovary cell CHO; a budding yeast, a fission yeast, a mold, a silkworm cell, or a *Xenopus oocyte* is generally used, however, any kind of eukaryotic cell may be used as long as it can express the FAD-conjugated glucose dehydrogenase. In order to introduce the expression vector into the eukaryotic cell, a known method such as an electroporation method, a calcium phosphate method, a liposome method, or a DEAF dextran method can be used.

In particular, self-cloning in which an appropriate *Aspergillus oryzae* strain is transformed with a recombinant vector containing a polynucleotide encoding the FAD-conjugated glucose dehydrogenase of the invention derived from *Aspergillus oryzae* is preferred.

In order to isolate and purify the target protein from a culture (such as microbial cells or a culture broth or a culture medium composition containing the enzyme secreted to the outside of microbial cells) after the FAD-conjugated glucose dehydrogenase is expressed in a prokaryotic cell or a eukaryotic cell, known separation procedures can be combined. Examples of such procedures include a treatment with a denaturant such as urea or a surfactant, a heat treatment, a pH treatment, an ultrasonication treatment, enzymatic digestion, salting out, a solvent sedimentation method, dialysis, centrifugal separation, ultrafiltration, gel filtration, SDS-PAGE, isoelectric focusing, ion exchange chromatography, hydrophobic chromatography, reverse-phase chromatography, and affinity chromatography (also including a method utilizing a tag sequence, and a method using a polyclonal antibody or a monoclonal antibody specific for the FAD coenzyme-conjugated glucose dehydrogenase).

Further, the FAD-conjugated glucose dehydrogenase can be obtained by a recombinant DNA technique using the polynucleotide (a cDNA or a coding region thereof) of the invention. For example, an RNA is prepared by in vitro transcription from a vector containing the above-mentioned polynucleotide, and in vitro translation is performed using the RNA as a template, whereby the FAD-conjugated glucose dehydrogenase can be obtained in vitro. Further, if the polynucleotide is recombined into a suitable expression vector by a known method, the FAD-conjugated glucose dehydrogenase encoded by the polynucleotide can be expressed in a large amount in a prokaryotic cell such as *Escherichia coli* or *Bacillus subtilis*; or a eukaryotic cell such as a yeast, a mold, an insect cell, or a mammalian cell. Further, a polynucleotide having the same amino acid sequence but having a codon usage optimized in accordance with the host may be introduced thereinto. Further, the host can be suitably selected in accordance with the need of a sugar chain or other peptide modification.

In the case where the FAD-conjugated glucose dehydrogenase is produced by expressing it in vitro, a recombinant vector is prepared by inserting the above-mentioned polynucleotide into a vector having a promoter to which an RNA polymerase can bind, and this vector is added to an in vitro translation system such as a rabbit reticulocyte lysate or a wheat germ extract including an RNA polymerase corresponding to the promoter, whereby the FAD-conjugated glucose dehydrogenase can be produced in vitro. Examples of the promoter to which an RNA polymerase can bind include T3, T7, and SP6. Examples of the vector containing such a promoter include pKA1, pCDM8, pT3/T718, pT7/319, and pBluescript II.

The recombinant FAD-conjugated glucose dehydrogenase of the invention can be produced by the method described above. Such an FAD-conjugated glucose dehydrogenase is an enzyme which catalyzes a reaction of the dehydrogenation of glucose in the presence of an electron acceptor, and therefore, the use thereof is not particularly limited as long as a change caused by this reaction can be utilized. For example, it can be used in the medical field or the clinical field such as the use in the determination of glucose in a sample containing a biological material, a reagent for use in the determination thereof, or a reagent for use in the elimination thereof, and also it can be used in the production of a substance using a coenzyme-conjugated glucose dehydrogenase.

The reagent composition for use in the determination of glucose of the invention may be formulated into a single reagent by mixing all the components, or in the case where the reagent composition contains components interfering with each other, the respective components are separated so as to provide suitable combinations. Further, the reagent composition may be prepared as a reagent in the form of a solution or a powder, and moreover, it may be prepared as a test paper or a film for use in the analysis by being incorporated in an appropriate support such as a filter paper or a film. Incidentally, a standard reagent containing a deproteinizing agent such as perchloric acid or a fixed amount of glucose may be attached. The amount of the enzyme in this composition is preferably about 0.1 to 50 units per sample. Examples of a specimen to be determined for glucose include plasma, serum, spinal fluid, saliva, and urine.

The biosensor of the invention is a glucose sensor which determines a glucose concentration in a sample liquid using a reaction layer containing the FAD-conjugated glucose dehydrogenase of the invention as an enzyme. The biosensor is produced by, for example, forming an electrode system comprising a working electrode, its counter electrode, and a reference electrode on an insulating base plate using a method such as screen printing, and forming an enzyme reaction layer containing a hydrophilic polymer, an oxidoreductase, and an electron acceptor on this electrode system in contact therewith. When a sample liquid containing a substrate is dropped on the enzyme reaction layer of this biosensor, the enzyme reaction layer is dissolved and the enzyme and the substrate are reacted with each other, and accompanying the reaction, the electron acceptor is reduced. After completion of the enzymatic reaction, the reduced electron acceptor is electrochemically oxidized. At this time, this biosensor can determine the substrate concentration in the sample liquid from the oxidation current value obtained. In addition, other than this, a biosensor of a type for detecting a coloring intensity or a pH change can also be constructed.

As the electron acceptor of the biosensor, a chemical substance having an excellent ability to donate and accept electrons can be used. The chemical substance having an excellent ability to donate and accept electrons is a chemical substance generally called "an electron carrier", "a mediator", or "a redox mediator", and as a chemical substance corresponding to such a substance, an electron carrier or a redox mediator cited in, for example, JP-T-2002-526759 or the like may be used. Specific examples thereof include an osmium compound, a quinone compound, and a ferricyan compound.

In the determination of the activity of the FAD-conjugated glucose dehydrogenase, the enzyme is preferably used by appropriately diluting it such that the final concentration thereof is 0.1 to 1.0 unit/mL. Incidentally, the unit of the enzymatic activity (unit) of the enzyme is an enzymatic activity that oxidizes 1 µmol of glucose per minute. The enzymatic activity of the FAD-conjugated glucose dehydrogenase of the invention can be determined by the following method.

[Method for Determination of Enzymatic Activity]

1.0 mL of 0.1 M potassium phosphate buffer (pH 7.0), 1.0 mL of 1.0 M D-glucose, 0.14 mL of 3 mM 2,6-dichlorophenol indophenol (hereinafter referred to as DCIP), 0.2 mL of 3 mM 1-methoxy-5-methylphenazinium methylsulfate, and 0.61 mL of water are added to a 3-mL quartz cell (light path length: 1 cm), and the cell is placed in a spectrophotometer provided with a thermostat cell holder and incubated at 37° C. for 5 minutes. Thereafter, 0.05 mL of an enzyme solution is added to the cell, and then, a change in the absorbance of DCIP at 600 nm (ΔABS/min) is determined. The molar extinction coefficient of DCIP at pH 7.0 is taken as $16.3 \times 10^3$ $cm^{-1}M^{-1}$, and the enzymatic activity to reduce 1 μmol of DCIP per minute is substantially equivalent to 1 unit of the enzymatic activity. Therefore, the enzymatic activity was determined from the change in the absorbance according to the following equation.

$$\text{Enzymatic activity (unit/mL)} = -\Delta ABS/16.3 \times 3.0/0.05 \times \text{Dilution ratio of enzyme} \quad \text{[Equation 1]}$$

In the determination of the protein concentration of this enzyme, the enzyme is preferably used by appropriately diluting it such that the final concentration thereof is 0.2 to 0.9 mg/mL. The protein concentration in the invention can be determined by the calculation from a calibration curve prepared using bovine serum albumin (BSA, manufactured by Wako Pure Chemical Industries, Ltd., for biochemical purpose) as a standard substance using a Bio-Rad Protein Assay, which is a protein concentration determination kit and can be purchased from Bio-Rad Laboratories, Inc. Japan according to the instruction attached to the kit.

Incidentally, various techniques used for implementing the invention can be easily and surely carried out by those skilled in the art based on publicly known documents and the like exclusive of techniques the sources of which are indicated specifically. For example, the genetic engineering and molecular biological techniques can be carried out based on the methods described in Sambrook and Maniatis, in Molecular Cloning: A Laboratory Manual, Cold Spring Harbor Laboratory Press, New York, 1989; Ausubel, F. M. et al., Current Protocols in Molecular Biology, John Wiley & Sons, New York, N.Y., 1995; and the like or the methods described in the references cited therein or methods substantially equivalent thereto or modified methods thereof. In addition, the terms in the invention are basically in accordance with IUPAC-IUB Commission on Biochemical Nomenclature or the meanings of terms conventionally used in the art.

Hereinafter, the invention will be more specifically described with reference to Examples. However, the technical scope of the invention is by no means limited to the description thereof. Further, the contents described in the documents cited in this description constitute the disclosure of this description as a part thereof.

EXAMPLE 1

Cloning of Gene Presumed to be FAD-Conjugated Glucose Dehydrogenase Derived from *Aspergillus oryzae* NBRC 5375 Strain into *Escherichia coli*

(1) Culture of Microbial Cells

A liquid culture medium containing 1% (w/v) glucose (manufactured by Nacalai Tesque), 2% (w/v) defatted soybean (manufactured by Showa Sangyo Co., Ltd.), 0.5% (w/v) corn steep liquor (manufactured by San-ei Sucrochemical Co., Ltd.), 0.1% (w/v) magnesium sulfate heptahydrate (manufactured by Nacalai Tesque), and water was adjusted to pH 6.0, and a 100 mL portion thereof was placed in a 500 mL Sakaguchi flask and autoclaved at 121° C. for 20 minutes. In the cooled liquid culture medium, *Aspergillus oryzae* NBRC 5375 strain was inoculated and subjected to shaking culture at 28° C. for 48 hours. Thereafter, the wet microbial cells (15.5 g) were collected using a centrifugal separator.

(2) Confirmation of Activity of FAD-Conjugated Glucose Dehydrogenase of *Aspergillus oryzae* NBRC 5375 Strain The microbial cells obtained in (1) were suspended in 50 mM potassium phosphate buffer (pH 7.5) and homogenized using sea sand B (manufactured by Nacalai Tesque). Then, the resulting homogenate was centrifuged and the supernatant was collected and used as a cell-free extract.

According to the above-mentioned method for the determination of enzymatic activity, the FAD-conjugated glucose dehydrogenase activity of the cell-free extract was confirmed, and the FAD-conjugated glucose dehydrogenase activity per cell-free extract was confirmed to be 0.0043 U/mL.

(3) Isolation of Total RNA

Among the microbial cells obtained in (1), 0.31 g of the wet microbial cells were frozen in liquid nitrogen, and then homogenized, and the total RNA was extracted using ISOGEN (manufactured by Nippon Gene Co., Ltd.).

(4) RT-PCR

RT-PCR was performed under the following conditions using a TaKaRa RNA LA PCR Kit (AMV) Ver. 1.1 (manufactured by Takara Bio Inc.), and PCR products containing a gene of about 1.8 kbp presumed to be an FAD-conjugated glucose dehydrogenase were obtained.

Template: Total RNA extracted in (3)
Primer:

Primer 1:
(SEQ ID NO: 6)
5'-tgggatcctatgctcttctcactggcat-3'

Primer 2:
(SEQ ID NO: 7)
5'-gccaagcttctaagcactcttcgcatcctccttaatcaagtc-3'

Incidentally, the primers 1 and 2 were synthesized based on the base sequence of AO090005000449 (presumed to be "a choline dehydrogenase") from the result of the gene analysis of *Aspergillus oryzae* NBRC 100959 strain disclosed in the above-mentioned DOGAN (Database of the Genomes Analyzed at NITE) (website http://www.bio.nite.go.jp/dogan/Top).

It is because the above-mentioned AO090005000449 was presumed not to be a choline dehydrogenase gene, but to be an FAD-conjugated glucose dehydrogenase gene of *Aspergillus oryzae* based on the base sequence information of an FAD-conjugated glucose dehydrogenase gene of *Aspergillus terreus* found by the present inventors.

Reaction conditions: Reverse transcription reaction at 42° C. for 30 minutes (1 cycle)
Denaturation at 99° C. for 5 minutes (1 cycle)
Cooling at 5° C. for 5 minutes (1 cycle)
Denaturation at 94° C. for 2 minutes (1 cycle)
Denaturation at 94° C. for 30 seconds, annealing at 45° C. for 30 seconds, and elongation reaction at 72° C. for 1 minute 30 seconds (25 cycles)
Elongation reaction at 72° C. for 5 minutes (1 cycle)

(5) Preparation of Plasmid Containing Gene Presumed to be FAD-Conjugated Glucose Dehydrogenase The PCR amplified fragments obtained in (4) were cleaved with restriction enzymes BamHI and HindIII, and ligated to a pUC18 vector (manufactured by Takara Bio, Inc.) treated with the same restriction enzymes using a DNA Ligation Kit Ver. 2.1 (manufactured by Takara Bio, Inc.), and a plasmid containing the gene presumed to be an FAD-conjugated glucose dehydrogenase was prepared.

(6) Production of Transformant

The plasmid obtained in (5) was introduced into *E. coli* JM109 Competent Cells (manufactured by Takara Bio, Inc.), and transformation was performed. The cells were cultured overnight in an LB plate containing ampicillin sodium (manufactured by Wako Pure Chemical Industries, Ltd.) at 37° C., and thereafter, it was confirmed that the plasmid containing the gene presumed to be an FAD-conjugated glucose dehydrogenase was introduced into one grown colony by direct PCR, and then, the transformant was obtained in the LB plate containing ampicillin sodium.

EXAMPLE 2

Cloning of Gene Presumed to be FAD-Conjugated Glucose Dehydrogenase Derived from *Aspergillus oryzae* NBRC 5375 Strain into *Aspergillus oryzae*

(1) Extraction of Chromosomal DNA

Among the wet microbial cells obtained in Example 1(1), a 0.25 g portion thereof was frozen in liquid nitrogen, and then homogenized, and a chromosomal DNA was extracted by a common procedure.

(2) Cloning of Gene Presumed to be FAD-Conjugated Glucose Dehydrogenase

As a host to be used, *Aspergillus oryzae* NS4 strain was used. This strain was bred in Brewery Laboratory in 1997 as described in a publicly known document 1 (Biosci. Biotech. Biochem., 61 (8), 1367-1369, 1997) and has been used in the analysis of transcription factors, the breeding of high-producing strains of various enzymes, and the like, and those for distribution are available.

For this strain, a modified amylase gene promoter derived from *Aspergillus oryzae* described in a publicly known document 2 (Development of the heterologous gene expression system for *Aspergillus* species, MINETOKI Toshitaka, Chemistry & Biology, 38, 12, pp. 831-838, 2000) was used, and a gene presumed to be an FAD-conjugated glucose dehydrogenase and amplified using the chromosomal DNA obtained in (1) as a template and also using the following primers synthesized based on the base sequence of AO090005000449 disclosed in DOGAN (Database of the Genomes Analyzed at NITE) (website http://www.bio.nite.go.jp/dogan/ Top) was ligated to downstream of the promoter, whereby a vector which can express this gene was prepared.

```
1. gene 1F:
                                         (SEQ ID NO: 8)
5'-(acgcgtcgac)tgaccaattccgcagctcgtcaaaatgctcttctc
actggcattcctga-3'

2. gene 1R:
                                         (SEQ ID NO: 9)
5'-(gtg)ctaagcactcttcgcatcctccttaatcaagtcgg-3'
```

(F is the 5' side, and R is the 3' side, bases in the parenthesis: restriction enzyme cleavage sites, underlined bases: enoA 5'-UTR, others: ORF)

Transformation was performed basically in accordance with the methods described in the publicly known document 2 and a publicly known document 3 (Genetic engineering technology of Koji mold for sake, GOMI Katsuya, Journal of the Brewing Society of Japan, pp. 494-502, 2000), whereby a transformant was obtained.

COMPARATIVE EXAMPLE

Cloning of Gene (AO090005000449) Presumed to be FAD-Conjugated Glucose Dehydrogenase Derived from *Aspergillus oryzae* NBRC 100959 Strain into *Aspergillus oryzae*

(1) Culture of Microbial Cells

A liquid culture medium containing 1% (w/v) glucose, 2% (w/v) defatted soybean, 0.5% (w/v) corn steep liquor, 0.1% (w/v) magnesium sulfate heptahydrate and water was adjusted to pH 6.0, and a 100 mL portion thereof was placed in a 500 mL Sakaguchi flask and autoclaved at 121° C. for 20 minutes. In the cooled liquid culture medium, *Aspergillus oryzae* NBRC 100959 strain was inoculated and subjected to shaking culture at 28° C. for 48 hours. Thereafter, the microbial cells (10.5 g) were collected using a centrifugal separator.

(2) Extraction of Chromosomal DNA

Among the microbial cells obtained in (1), 0.31 g of the wet microbial cells were frozen in liquid nitrogen, and then homogenized, and a chromosomal DNA was extracted by a common procedure.

(3) Cloning of Gene (AO090005000449 Gene) Presumed to be FAD-Conjugated Glucose Dehydrogenase As a host to be used, *Aspergillus oryzae* NS4 strain was used. This strain was bred in Brewery Laboratory in 1997 as described in the publicly known document 1, and has been used in the analysis of transcription factors, the breeding of high-producing strains of various enzymes, and the like, and those for distribution are available.

For this strain, a modified amylase gene promoter derived from *Aspergillus oryzae* described in the publicly known document 2 was used, and a gene (AO090005000449 gene) presumed to be an FAD-conjugated glucose dehydrogenase and amplified using the chromosomal DNA obtained in (2) as a template and also using the primers (SEQ ID NOS: 8 and 9) used in Example 2 was ligated to downstream of the promoter, whereby a vector which can express this gene was prepared.

Transformation was performed basically in accordance with the methods described in the publicly known documents 2 and 3, whereby a transformant was obtained.

EXAMPLE 3

Confirmation of Gene Sequence (1) Sequence of Gene Presumed to be FAD-Conjugated Glucose Dehydrogenase Derived from *Aspergillus oryzae* NBRC 5375 Strain in Recombinant *Escherichia coli*

The sequence determination of the gene presumed to be an FAD-conjugated glucose dehydrogenase derived from *Aspergillus oryzae* NBRC 5375 strain in the recombinant *Escherichia coli* obtained in Example 1 was performed, and the result is shown in SEQ ID NO: 3. The sequence shown in SEQ ID NO: 3 was compared with a cDNA sequence obtained by removing the intron from the base sequence of the gene (AO090005000449) presumed to be an FAD-conjugated glucose dehydrogenase in Comparative example, and it was found that the sequence of ATG at positions 604 to 606 with the start base A of AO090005000449 counted as position 1 was different from that of the gene presumed to be an FAD-conjugated glucose dehydrogenase derived from *Aspergillus oryzae* NBRC 5375 strain which had the sequence of GCTGGTGTTCCATGGGTT represented by SEQ ID NO: 5 instead, and the other sequences agreed completely with each other.

Further, the translated amino acid sequence is shown in SEQ ID NO: 1, and a comparison of the amino acid sequences was made in the same manner, and it was found that the amino acid residue M at position 202 with the start amino acid residue M of AO090005000449 counted as position 1 was different from that of the amino acid sequence encoded by the gene presumed to be an FAD-conjugated glucose dehydrogenase derived from *Aspergillus oryzae* NBRC 5375 strain which had the sequence of AGVPWV represented by SEQ ID NO: 4 instead, and the other sequences agreed completely with each other.

(2) Sequence of Gene Presumed to be FAD-Conjugated Glucose Dehydrogenase Derived from *Aspergillus oryzae* NBRC 5375 Strain in Recombinant Mold The sequence determination of the gene presumed to be an FAD-conjugated glucose dehydrogenase derived from *Aspergillus oryzae* NBRC 5375 strain in the recombinant mold obtained in Example 2 was performed, and the result is shown in SEQ ID NO: 2. The sequence shown in SEQ ID NO: 2 was compared with the base sequence of the gene (AO090005000449) presumed to be an FAD-conjugated glucose dehydrogenase in Comparative example, and it was found that the sequence of ATG at positions 656 to 658 with the start base A of AO090005000449 counted as position 1 was different from that of the gene presumed to be an FAD-conjugated glucose dehydrogenase derived from *Aspergillus oryzae* NBRC 5375 strain which had the sequence of GCTGGTGTTCCATGGGTT represented by SEQ ID NO: 5 instead.

Further, the translated amino acid sequence is shown in SEQ ID NO: 1 and a comparison of the amino acid sequences was made in the same manner, and it was found that the amino acid residue M at position 202 with the start amino acid residue M of AO090005000449 (presumed to be a choline dehydrogenase) counted as position 1 was different from that of the amino acid sequence encoded by the gene presumed to be an FAD-conjugated glucose dehydrogenase derived from *Aspergillus oryzae* NBRC 5375 strain which had the sequence of AGVPWV represented by SEQ ID NO: 4 instead, and the other sequences agreed completely with each other.

(Comparison of Gene Sequences)

From the above results, it was found that in the strains of Examples 1 and 2 and the strain of Comparative example, the genes presumed to be an FAD-conjugated glucose dehydrogenase had a similar gene sequence, however, as compared with the sequence of the gene of AO090005000449 derived from the strain of Comparative example, the sequence of the gene derived from *Aspergillus oryzae* NBRC 5375 strain in each of Examples 1 and 2 had the sequence of GCTGGTGTTCCATGGGTT represented by SEQ ID NO: 5 in place of the sequence of ATG at positions 656 to 658. Further, when a comparison of the amino acid sequences was made, it was found that the amino acid sequence encoded by the gene derived from *Aspergillus oryzae* NBRC 5375 strain had AGVPWV represented by SEQ ID NO: 4 in place of the amino acid residue M in the vicinity of position 202 of AO090005000449.

EXAMPLE 4

Analysis and Comparison at Gene Level (1) Confirmation by Southern Blotting

From wet microbial cells cultured using each of the strains obtained in Example 2 and Comparative example, DNA was extracted by a common procedure, and detection was performed by Southern blotting using a part of the gene presumed to be the FAD-conjugated glucose dehydrogenase as a probe.

As a result, it was found that in each of the strains, a DNA fragment containing the gene presumed to be the FAD-conjugated glucose dehydrogenase ligated to the modified amylase gene promoter derived from *Aspergillus oryzae* was contained in substantially the same copy number.

That is, it was found that in each of the strains obtained in Example 2 and Comparative example, the gene was contained in substantially the same copy number by transformation.

(2) Confirmation by Northern Blotting

From wet microbial cells cultured using each of the strains obtained in Example 2 and Comparative example, RNA was extracted by a common procedure, and detection was performed by Northern blotting using a part of the gene presumed to be the FAD-conjugated glucose dehydrogenase as a probe.

As a result, it was found that in each of the strains, which were transformed a mRNA fragment presumed to be derived from the FAD-conjugated glucose dehydrogenase gene ligated to the modified amylase gene promoter derived from *Aspergillus oryzae* was detected to substantially the same extent. That is, it could be determined that in each of the strains obtained in Example 2 and Comparative example, the gene presumed to be the FAD-conjugated glucose dehydrogenase was transcribed into an RNA to substantially the same extent.

EXAMPLE 5

Confirmation of FAD-Conjugated Glucose Dehydrogenase Activity in Transformed Strain The microbial cells of Example 1 were subjected to shaking culture in an LB liquid culture medium containing 50 μg/mL ampicillin sodium and 0.1 mM isopropyl-β-D-1-thiogalactopyranoside (manufactured by Sigma-Aldrich Japan KK) at 37° C. for 17 hours. After completion of the culture, the microbial cells were collected, suspended in 50 mM potassium phosphate buffer (pH 7.0), and homogenized using an ultrasonic homogenizer. Then, the resulting homogenate was centrifuged and the supernatant was collected, whereby a cell-free extract was obtained.

When the cell-free extract was subjected to SDS-PAGE, an enzyme protein having a molecular weight of about 63 kDa could be confirmed, and the FAD-conjugated glucose dehydrogenase activity per cell-free extract was confirmed to be 0.014 U/mL. Incidentally, this activity was not at all confirmed in *Escherichia coli* used as the host.

The microbial cells of each of Example 2 and Comparative example were subjected to shaking culture at 28° C. for 3 days in a liquid culture medium containing 1% peptone, 2% sucrose, 0.5% dipotassium hydrogen phosphate, and 0.05% magnesium sulfate. After completion of the culture, the microbial cells and the culture supernatant were collected by centrifugation. The microbial cells were suspended in 50 mM potassium phosphate buffer (pH 7.0) and homogenized using a chip-type ultrasonic homogenizer. Then, the resulting homogenate was centrifuged and the supernatant was collected and used as a cell-free extract.

When the culture supernatant and the cell-free extract were subjected to SDS-PAGE, in the case of the microbial cells of Example 2, an enzyme protein having a molecular weight of about 86 kDa could be confirmed in the culture supernatant, however, in the case of the microbial cells of Comparative example, the protein could not be confirmed in the culture supernatant or the cell-free extract.

Further, in accordance with the above-mentioned method for the determination of enzymatic activity, the FAD-conjugated glucose dehydrogenase activity in the culture supernatant and the cell-free extract was confirmed, and in the case of the microbial cells of Example 2, the FAD-conjugated glucose dehydrogenase activity of 53 U/mL was confirmed in the culture supernatant, however, in the case of the microbial cells of Comparative example, the activity could not be confirmed at all in the culture supernatant or the cell-free extract.

(Conclusion)

When summarizing the findings of Examples 3 to 5, it can be concluded that although Example 2 and Comparative example are comparable in terms of the transformed gene copy number and its transcription level, the sequences presumed to be the gene of the FAD-conjugated glucose dehydrogenase transformed are subtly different, and the difference between the gene sequences largely affects the expression of the enzymatic activity.

EXAMPLE 6

Comparison Among Other *Aspergillus oryzae* Strains

For several other *Aspergillus oryzae* strains, the FAD-conjugated glucose dehydrogenase activity in the culture supernatant and the cell-free extract (CFE) was confirmed in the same manner as in Example 1-(2). Further, for each of these strains, a chromosomal DNA was extracted in the same manner as in Example 2-(1), and the sequence of a fragment of about 1.9 kbp amplified using the primers represented by SEQ ID NOS: 6 and 7 was determined and compared with the sequence represented by SEQ ID NO: 2 and with the chromosomal DNA sequence of AO090005000449. Further, the translated amino acid sequence was compared with the sequence represented by SEQ ID NO: 1 and with the amino acid sequence of AO090005000449. These results are shown in the following Table 1 along with the results of Examples 1 to 3 and Comparative example. As for the sequence, particularly, the presence or absence of the amino acid sequence of AGVPWV described in Example 3-(1) is shown in Table 1.

TABLE 1

| Strain (*Aspergillus oryzae*) | Presence or absence of FAD-conjugated glucose dehydrogenase activity in culture supernatant or CFE | Presence or absence of amino acid sequence: AGVPWV |
|---|---|---|
| NBRC 5375 | Presence | Presence |
| NBRC 100959 | Absence | Absence |
| NBRC 4079 | Presence | Presence |
| NBRC 4203 | Presence | Presence |
| NBRC 4214 | Presence | Presence |
| NBRC 4268 | Presence | Presence |
| NBRC 5238 | Presence | Presence |
| NBRC 6215 | Presence | Presence |
| NBRC 30104 | Presence | Presence |
| NBRC 30113 | Presence | Presence |
| NBRC 4181 | Absence | Absence |
| NBRC 4220 | Absence | Absence |

All of the chromosomal DNA sequences derived from *Aspergillus oryzae* NBRC 4079, 4214, 4268, 5238, 6215, and 30113 agreed completely with the sequence represented by SEQ ID NO: 2.

The chromosomal DNA sequence derived from *Aspergillus oryzae* NBRC 4203 was different in four bases (135C→A, 437G→A, 532G→A, 1263C→T) from the sequence represented by SEQ ID NO: 2. Further, the amino acid sequence translated from the chromosomal DNA sequence derived from *Aspergillus oryzae* NBRC 4203 was different in two amino acid residues (129V→I, 386A→V) from the sequence represented by SEQ ID NO: 1.

Further, the chromosomal DNA sequence derived from *Aspergillus oryzae* NBRC 30104 was different in four bases (135C→A, 413C→A, 437G→A, 532G→A) from the sequence represented by SEQ ID NO: 2. Further, the amino acid sequence translated from the chromosomal DNA sequence derived from *Aspergillus oryzae* NBRC 30104 was different in two amino acid residues (121R→S, 129V→I) from the sequence represented by SEQ ID NO: 1. It was considered that the difference between these amino acid sequences did not directly affect the expression of the FAD-conjugated glucose dehydrogenase.

Further, both of the chromosomal DNA sequences derived from *Aspergillus oryzae* NBRC 4181 and 4220 agreed completely with the chromosomal DNA sequence of AO090005000449.

From the results of Examples 1 to 5 and Comparative example, it was concluded that the gene presumed to be an FAD-conjugated glucose dehydrogenase derived from *Aspergillus oryzae* NBRC 5375 strain was a gene encoding an active form of an FAD-conjugated glucose dehydrogenase, and also that the gene presumed to be an FAD-conjugated glucose dehydrogenase derived from *Aspergillus oryzae* NBRC 100959 strain (AO090005000449 gene) was not a gene encoding an active form of an FAD-conjugated glucose dehydrogenase. The AO090005000449 gene encodes the amino acid sequence very similar to that of an FAD-conjugated glucose dehydrogenase derived from NBRC 5375 strain, and therefore, in the light of the technical common knowledge in this technical field, it is assumed that the enzyme has a similar enzymatic activity. However, it was unexpectedly found for the first time by the present inventors that, in fact, as shown in Comparative example, the enzyme was not expressed by the sequences of the AO090005000449 gene, NBRC 4181 gene, and 4220 gene. Even though a similar expression system was used, the FAD-conjugated glucose dehydrogenase was expressed or not expressed depending only on the difference of the above-mentioned sequence. Therefore, though it is only a hypothesis, the amino acid sequence: AGVPWV contained in the FAD-conjugated glucose dehydrogenase derived from *Aspergillus oryzae* NBRC 5375 strain or the like is considered to be an important sequence for forming the conformation of the FAD-conjugated glucose dehydrogenase, and it is presumed that when the sequence of AGVPWV is lacking, endoplasmic reticulum stress or the like occurs to cause the degradation of the expressed protein and/or the suppression of the expression of the protein. The presence of the amino acid sequence: AGVPWV in the vicinity of position 202 with the initiator amino acid residue M counted as position 1 is important for expressing the function. In this connection, which amino acid residue in this sequence is essential for expressing the activity is currently being studied, however, there is a possibility that even if a part of the amino acid residues are lost, substituted, or added, the activity can be maintained to some extent. Further, as for the region other than the amino acid sequence: AGVPWV, substitution of several amino acid residues found from the analysis of the genes of *Aspergillus oryzae* NBRC 4203 and *Aspergillus oryzae* NBRC 30104 did not affect the expression of the FAD-conjugated glucose dehydrogenase.

EXAMPLE 7

Test for Properties of FAD-Conjugated Glucose Dehydrogenase

The culture supernatant of the microbial cells of Example 2 obtained in Example 5 was concentrated with Vivacell 2 having a fractionation molecular weight of 10000 (manufactured by Vivascience, Inc.), and then replaced with distilled water, whereby a purified enzyme having a specific activity per protein of 323 U/mg was obtained. Incidentally, enzymes derived from other strains showing an FAD-conjugated glucose dehydrogenase activity could be purified in the same manner. When these purified enzymes were subjected to SDS-PAGE, a single band of about 86 kDa could be confirmed. This enzyme was examined for its activity, substrate specificity, and coenzyme. The enzymatic activity was determined according to the above-mentioned method for the determination of enzymatic activity.

1) Activity

The purified enzyme was reacted with 500 mM D-glucose in the presence of 8.66 mM DCIP, and the reaction product was determined using a D-gluconic acid/D-glucono-δ-lactone assay kit. As a result, the production of D-gluconic acid was confirmed, and accordingly, it was revealed that the FAD-conjugated glucose dehydrogenase of the invention was an enzyme which catalyzed a reaction of the oxidation of a hydroxy group at the 1-position of D-glucose.

2) Substrate Specificity

As a substrate in a reaction solution for the determination of activity in the above-mentioned method for the determination of enzymatic activity, D-glucose, maltose, and D-galactose were used, and the enzymatic activity of the purified enzyme was determined according to the method for the determination of enzymatic activity. The enzyme had an activity such that the value of enzymatic activity for maltose was 2.1% and the value of enzymatic activity for D-galactose was 0.99% with the value of enzymatic activity for D-glucose taken as 100%.

3) Coenzyme

D-glucose was added to the purified enzyme, and absorption spectroscopy was performed. As a result, the absorption maxima observed at 385 nm and 465 nm disappeared by the addition, and therefore, it was revealed that the coenzyme was FAD.

EXAMPLE 8

Determination of Glucose with Enzyme-Immobilized Electrode

By using the purified enzyme described in Example 7, the determination of D-glucose with an enzyme-immobilized electrode was performed. By using a glassy carbon (GC) electrode on which 1.5 U of this enzyme was immobilized, a response current to the glucose concentration was determined. To an electrolytic cell, 1.8 mL of 50 mM potassium phosphate buffer (pH 6.0) and 0.2 mL of a 1 M aqueous solution of potassium hexacyanoferrate(III) (potassium ferricyanide) were added. The GC electrode was connected to a potentiostat BAS 100B/W (manufactured by BAS, Inc.), and the solution was stirred at 37° C., and +500 mV was applied to a silver-silver chloride reference electrode. To such a system, a 1 MD-glucose solution was added such that the final concentration of D-glucose became 5, 10, 20, 30, 40, or 50 mM, and a current in a steady state was determined for each addition operation. The current values were plotted against the known glucose concentrations (5, 10, 20, 30, 40, and 50 mM), whereby a calibration curve was prepared (FIG. 1). From this, it was shown that glucose could be quantitatively determined with an enzyme-immobilized electrode using the FAD-conjugated glucose dehydrogenase of the invention.

EXAMPLE 9

Confirmation of FAD-Conjugated Glucose Dehydrogenase Gene by PCR (1) Culture of Microbial Cells A liquid culture medium containing 1% (w/v) glucose (manufactured by Nacalai Tesque), 2% (w/v) defatted soybean (manufactured by Showa Sangyo Co., Ltd.), 0.5% (w/v) corn steep liquor (manufactured by San-ei Sucrochemical Co., Ltd.), 0.1% (w/v) magnesium sulfate heptahydrate (manufactured by Nacalai Tesque) and water was adjusted to pH 6.0, and a 10 mL portion thereof was placed in a large diameter test tube and autoclaved at 121° C. for 20 minutes. In the cooled liquid culture medium, as shown in Example 4, *Aspergillus oryzae* NBRC 4268 strain, NBRC 5375 strain, and NBRC 6215 strain confirmed to have a glucose dehydrogenase activity in the culture broth, and *Aspergillus oryzae* NBRC 4181 strain, NBRC 4220 strain, and NBRC 100959 strain confirmed to have no glucose dehydrogenase activity in the culture broth were inoculated in the respective test tubes and subjected to shaking culture at 30° C. for 43 hours. Thereafter, the wet microbial cells were collected using a centrifugal separator, respectively.

(2) Extraction of Chromosomal DNA

The wet microbial cells obtained in (1) were frozen in liquid nitrogen, and then homogenized, and a chromosomal DNA was extracted by a common procedure.

(3) Amplification of Full-Length FAD-Conjugated Glucose Dehydrogenase Gene

PCR was performed under the following conditions using each DNA extracted in (2) as a template and also using primers 3 and 4 synthesized based on the sequence represented by SEQ ID NO: 2, and PCR products containing an FAD-conjugated glucose dehydrogenase gene of about 1.9 kbp were obtained.

Template: DNA extracted in (2)

Primers:

```
Primer 3:
                                        (SEQ ID NO: 10)
5'-ttatgctcttctcactggcattcctgagtgccctgt-3'

Primer 4:
                                        (SEQ ID NO: 11)
5'-gctaagcactcttcgcatcctccttaatcaagtcgg-3'
```

Reaction conditions: Denaturation at 94° C. for 1 minute (1 cycle)

Denaturation at 94° C. for 30 seconds, annealing at 45° C. for 30 seconds, and elongation reaction at 72° C. for 1 minute 30 seconds (30 cycles)

Elongation reaction at 72° C. for 10 minutes (1 cycle)

(4) Amplification of Gene of FAD-Conjugated Glucose Dehydrogenase Expressing Activity PCR was performed under the following conditions using each PCR product obtained in (3) as a template and also using the primer 3 and a primer 5 synthesized based on the amino acid sequence: AGVPWV.

Template: PCR product obtained in (3)
Primers:

```
Primer 3:
                                       (SEQ ID NO: 10)
5'-ttatgctcttctcactggcattcctgagtgccctgt-3'

Primer 5:
                                       (SEQ ID NO: 12)
5'-aacccatggaacaccagc-3'
```

Reaction conditions: Denaturation at 94° C. for 1 minute (1 cycle)

Denaturation at 94° C. for 30 seconds, annealing at 65° C. for 30 seconds, and elongation reaction at 72° C. for 1 minute (30 cycles)

Elongation reaction at 72° C. for 5 minutes (1 cycle)

Figure 2:
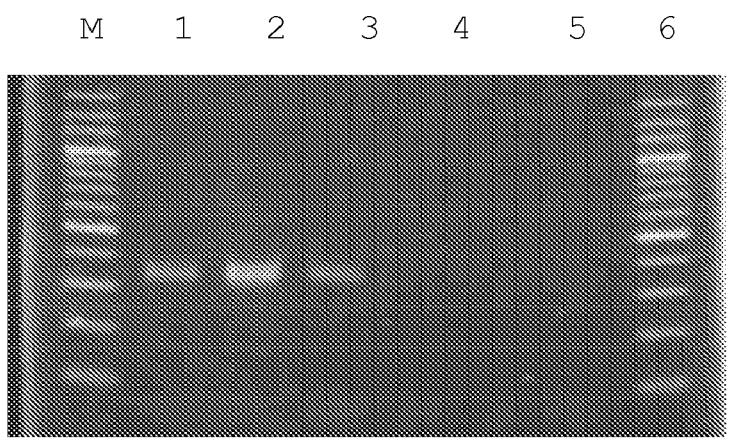
FIG. 2 shows the detection results of a target gene by PCR. The symbols in the drawing are as follows. M: 200 bp DNA ladder marker (manufactured by Takara Bio Inc.); 1: *Aspergillus oryzae* NBRC4268; 2: *Aspergillus oryzae* NBRC 5375; 3: *Aspergillus oryzae* NBRC 6215; 4: *Aspergillus oryzae* NBRC 4181; 5: *Aspergillus oryzae* NBRC 4220; 6: *Aspergillus oryzae* NBRC 100959

The results of the detection of the target gene by PCR are shown in FIG. 2. It could be confirmed that only the polynucleotide encoding the FAD-conjugated glucose dehydrogenase derived from *Aspergillus oryzae* having a glucose dehydrogenase activity in the culture broth was amplified with a size as predicted by PCR. Incidentally, even when PCR was performed using the DNA obtained in (2) directly as the template, it could be confirmed that only the polynucleotide encoding the FAD-conjugated glucose dehydrogenase derived from *Aspergillus oryzae* having a glucose dehydrogenase activity in the culture broth was amplified with a size as predicted by PCR in the same manner.

EXAMPLE 10

Confirmation of FAD-Conjugated Glucose Dehydrogenase Gene by Southern Hybridization 100 ng of each PCR product obtained in Example 10 (1) was subjected to agarose gel electrophoresis, followed by blotting onto a nylon membrane (Hybond-N+, manufactured by GE Health Care, Inc.), and the membrane was treated at 80° C. for 71 hours for fixation. After prehybridization, a probe synthesized based on the amino acid sequence: AGVPWV and fluorescently labeled with fluorescein isothiocyanate (FITC) at the 5'-terminus was added thereto, and the membrane was incubated at 37° C. for 24 hours. Then, the membrane was washed at 4° C. with 6×SSC and at 50° C. with a tetramethylammonium chloride solution, and thereafter, SDS derived from the tetramethylammonium chloride solution was washed off with 25 mM TBS. Then, fluorescent detection was performed using an image analyzer (Typhoon 9400, manufactured by GE Health Care, Inc.). The composition of the buffer used and the sequence of the probe used are shown below.

Hybridization Buffer:
6×SSC
5×Denhardt's solution
0.5% skim milk
20×SSC:
3 M sodium chloride
0.3 M trisodium citrate
Tetramethylammonium Chloride Solution:
3 M tetramethylammonium chloride
50 mM Tris-HCl (pH 8.0)
2 mM EDTA
0.1% SDS

```
                                       (SEQ ID NO: 5)
Probe: 5'(FITC)-gctggtgttccatgggtt-3'
```

Figure 3:
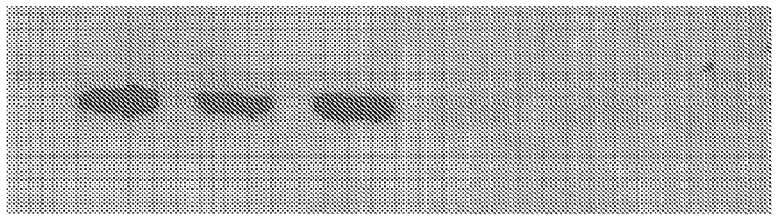
FIG. 3 shows the detection results of a target gene by Southern hybridization. The symbols in the drawing are the same as in FIG. 2.

The results of the detection of the target gene by Southern hybridization are shown in FIG. 3. It is found that only the polynucleotide encoding the FAD-conjugated glucose dehydrogenase derived from *Aspergillus oryzae* having a glucose dehydrogenase activity in the culture broth could be detected by Southern hybridization. Incidentally, even when the confirmation by Southern hybridization is performed by immobilizing the PCR product obtained in (3) on a nylon membrane (Hybond-N+, manufactured by GE Health Care, Inc.), the same results can be obtained.

EXAMPLE 11

Cloning of Gene that could be Confirmed to be FAD-Conjugated Glucose Dehydrogenase Gene and Secretion and Production in Cloned Strain According to the method described in Example 2, the gene which could be confirmed to be the polynucleotide encoding the FAD-conjugated glucose dehydrogenase derived from *Aspergillus oryzae* capable of secreting and producing the glucose dehydrogenase in the culture broth by the method shown in Example 9 and/or Example 10 was ligated to a vector, the resulting recombinant vector was cloned into a strain, and then, the cloned strain was cultured. As a result, in a culture supernatant, an active form of the enzyme could be secreted and produced in a large amount.

EXAMPLE 12

Confirmation of Amino Acid Residue that Affects Expression of Activity of FAD-Conjugated Glucose Dehydrogenase Derived from *Aspergillus oryzae*

Several mutated enzyme genes in which one amino acid residue among the six amino acid residues (AGVPWV (the amino acid residues 202 to 207)) of the FAD-conjugated glucose dehydrogenase derived from *Aspergillus oryzae* NBRC 5375 strain was deleted, a mutated enzyme gene in which all of the six amino acid residues were deleted, and a mutated enzyme gene having the bases encoding Met in place of these six amino acid residues were prepared, and each of the mutated genes was introduced into *Aspergillus oryzae* NS4 strain, and the effect on the expression of the activity was confirmed. Incidentally, the preparation of the mutated genes were performed using a Quikchange Site-Directed Mutagenesis kit manufactured by Stratagene, Inc., and the introduction of the gene into *Aspergillus oryzae* was performed according to the method described in Example 2. The average of the activity values (3 strains) per culture medium was calculated for each of the recombinants (presumed to contain a single copy) into which the respective mutated genes were introduced, and the results are shown in Table 2. From these results, it is strongly suggested that for the expression of the activity of the FAD-conjugated glucose dehydrogenase derived from *Aspergillus oryzae*, these six amino acid residues, particularly the amino acid residues 205 to 207 were important.

TABLE 2

| No. | Mutation site (deletion of amino acid residue) | Activity value (U/mL) | Relative activity (%) with the activity of Control (No. 1) taken as 100 |
|---|---|---|---|
| 1 | Non (Control) | 42 | 100 |
| 2 | 205 (Pro) | 0.04 | 0.1 or less |
| 3 | 206 (Trp) | 0.03 | 0.1 or less |
| 4 | 207 (Val) | 0.04 | 0.1 or less |
| 5 | 202 to 207 (Ala-Gly-Val-Pro-Trp-Val) | 0.02 | 0.1 or less |
| 6 | Met is introduced into the deletion site of No. 8 in place of 6 amino acid residues (corresponding to gene of AO090005000449 of Comparative example) | 0.03 | 0.1 or less |

Industrial Applicability

An FAD-conjugated glucose dehydrogenase encoded by a polynucleotide of the invention does not substantially act on maltose in the determination of blood glucose, and therefore can be utilized also in a self-monitoring of blood glucose (SMBG) device with higher accuracy, and largely contributes to self-care and self-treatment by patients with diabetes.

---

The invention claimed is:

1. A biosensor comprising a recombinant FAD-conjugated glucose dehydrogenase, wherein the recombinant FAD-conjugated glucose dehydrogenase is selected from the group consisting of:
- (a) a polypeptide which comprises the amino acid sequence represented by SEQ ID NO: 1; and
- (b) a polypeptide which comprises an amino acid sequence having a homology of 90% or more to the amino acid sequence (a) and has an FAD-conjugated glucose dehydrogenase activity, and wherein the biosensor is capable of detecting glucose.

2. The biosensor of claim 1, wherein the biosensor comprises a reaction layer comprising the recombinant FAD-conjugated glucose dehydrogenase.

3. The biosensor of claim 2, wherein the reaction layer further comprises a hydrophilic polymer and an electron acceptor.

4. The biosensor of claim 3, wherein the electron receptor is an osmium compound, a quinone compound or a ferricyan compound.

5. The biosensor of claim 3, wherein the reaction layer is in contact with an electrode system comprising a working electrode, a counter electrode, and a reference electrode, each on an insulating base plate.

6. The biosensor of claim 1, which is capable of detecting glucose by detection of an oxidation current.

7. The biosensor of claim 1, which is capable of detecting glucose by a change in color intensity.

8. The biosensor of claim 1, which is capable of detecting glucose by a pH change.

9. A method of making a biosensor, comprising:
- forming an electrode system comprising a working electrode, a counter electrode, and a reference electrode, each on an insulating base plate, and
- forming a reaction layer on the electrode system comprising a hydrophilic polymer, the recombinant FAD-conjugated glucose dehydrogenase of claim 1, and an electron receptor.

10. The process of making a biosensor of claim 9, wherein the electron receptor is an osmium compound, a quinone compound or a ferricyan compound.

* * * * *

SEQUENCE LISTING

<160> NUMBER OF SEQ ID NOS: 12

<210> SEQ ID NO 1
<211> LENGTH: 593
<212> TYPE: PRT
<213> ORGANISM: Aspergillus oryzae NBRC5375

<400> SEQUENCE: 1

```
Met Leu Phe Ser Leu Ala Phe Leu Ser Ala Leu Ser Leu Ala Thr Ala
1               5                   10                  15

Ser Pro Ala Gly Arg Ala Lys Asn Thr Thr Thr Tyr Asp Tyr Ile Val
                20                  25                  30

Val Gly Gly Gly Thr Ser Gly Leu Val Val Ala Asn Arg Leu Ser Glu
            35                  40                  45

Asn Pro Asp Val Ser Val Leu Leu Leu Glu Ala Gly Ala Ser Val Phe
        50                  55                  60

Asn Asn Pro Asp Val Thr Asn Ala Asn Gly Tyr Gly Leu Ala Phe Gly
65                  70                  75                  80

Ser Ala Ile Asp Trp Gln Tyr Gln Ser Ile Asn Gln Ser Tyr Ala Gly
                85                  90                  95

Gly Lys Gln Gln Val Leu Arg Ala Gly Lys Ala Leu Gly Gly Thr Ser
                100                 105                 110

Thr Ile Asn Gly Met Ala Tyr Thr Arg Ala Glu Asp Val Gln Ile Asp
            115                 120                 125

Val Trp Gln Lys Leu Gly Asn Glu Gly Trp Thr Trp Lys Asp Leu Leu
        130                 135                 140

Pro Tyr Tyr Leu Lys Ser Glu Asn Leu Thr Ala Pro Thr Ser Ser Gln
145                 150                 155                 160

Val Ala Ala Gly Ala Ala Tyr Asn Pro Ala Val Asn Gly Lys Glu Gly
                165                 170                 175

Pro Leu Lys Val Gly Trp Ser Gly Ser Leu Ala Ser Gly Asn Leu Ser
                180                 185                 190

Val Ala Leu Asn Arg Thr Phe Gln Ala Ala Gly Val Pro Trp Val Glu
            195                 200                 205

Asp Val Asn Gly Gly Lys Met Arg Gly Phe Asn Ile Tyr Pro Ser Thr
        210                 215                 220
```

Leu Asp Val Asp Leu Asn Val Arg Glu Asp Ala Ala Arg Ala Tyr Tyr
225                 230                 235                 240

Phe Pro Tyr Asp Asp Arg Lys Asn Leu His Leu Leu Glu Asn Thr Thr
            245                 250                 255

Ala Asn Arg Leu Phe Trp Lys Asn Gly Ser Ala Glu Gly Ala Ile Ala
        260                 265                 270

Asp Gly Val Glu Ile Thr Ser Ala Asp Gly Lys Val Thr Arg Val His
    275                 280                 285

Ala Lys Lys Glu Val Ile Ile Ser Ala Gly Ala Leu Arg Ser Pro Leu
290                 295                 300

Ile Leu Glu Leu Ser Gly Val Gly Asn Pro Thr Ile Leu Lys Lys Asn
305                 310                 315                 320

Asn Ile Thr Pro Arg Val Asp Leu Pro Thr Val Gly Glu Asn Leu Gln
            325                 330                 335

Asp Gln Phe Asn Asn Gly Met Ala Gly Glu Gly Tyr Gly Val Leu Ala
        340                 345                 350

Gly Ala Ser Thr Val Thr Tyr Pro Ser Ile Ser Asp Val Phe Gly Asn
    355                 360                 365

Glu Thr Asp Ser Ile Val Ala Ser Leu Arg Ser Gln Leu Ser Asp Tyr
370                 375                 380

Ala Ala Ala Thr Val Lys Val Ser Asn Gly His Met Lys Gln Glu Asp
385                 390                 395                 400

Leu Glu Arg Leu Tyr Gln Leu Gln Phe Asp Leu Ile Val Lys Asp Lys
            405                 410                 415

Val Pro Ile Ala Glu Ile Leu Phe His Pro Gly Gly Asn Ala Val
        420                 425                 430

Ser Ser Glu Phe Trp Gly Leu Leu Pro Phe Ala Arg Gly Asn Ile His
    435                 440                 445

Ile Ser Ser Asn Asp Pro Thr Ala Pro Ala Ala Ile Asn Pro Asn Tyr
450                 455                 460

Phe Met Phe Glu Trp Asp Gly Lys Ser Gln Ala Gly Ile Ala Lys Tyr
465                 470                 475                 480

Ile Arg Lys Ile Leu Arg Ser Ala Pro Leu Asn Lys Leu Ile Ala Lys
            485                 490                 495

Glu Thr Lys Pro Gly Leu Ser Glu Ile Pro Ala Thr Ala Ala Asp Glu
        500                 505                 510

Lys Trp Val Glu Trp Leu Lys Ala Asn Tyr Arg Ser Asn Phe His Pro
    515                 520                 525

Val Gly Thr Ala Ala Met Met Pro Arg Ser Ile Gly Val Val Asp
530                 535                 540

Asn Arg Leu Arg Val Tyr Gly Thr Ser Asn Val Arg Val Val Asp Ala
545                 550                 555                 560

Ser Val Leu Pro Phe Gln Val Cys Gly His Leu Val Ser Thr Leu Tyr
            565                 570                 575

Ala Val Ala Glu Arg Ala Ser Asp Leu Ile Lys Glu Asp Ala Lys Ser
        580                 585                 590

Ala

<210> SEQ ID NO 2
<211> LENGTH: 1941
<212> TYPE: DNA
<213> ORGANISM: Aspergillus oryzae NBRC5375

<400> SEQUENCE: 2

-continued

```
atgctcttct cactggcatt cctgagtgcc ctgtcgctgg ccacggcatc accggctgga     60
cgggccaaga acactacgac atacgactac atcgttgtgg gaggcggcac aagtggtctt    120
gtggtcgcaa atcgcctttc tgagaacccc gatgtctccg ttcttctgct tgaggccggt    180
gcttctgtgt caacaaccc ggacgtaacc aacgctaacg gttatggatt ggccttttggc   240
tcggccatcg actggcagta ccagtctatt aaccaaagct atgcaggagg taaacagcaa    300
gttctgcgtg ctggtaaggc ccttggagga accagtacaa tcaatggtat gcttctatgg    360
atgatctctt agtcggcatg gaccactgac gaccacagga atggcctata cccgcgcaga    420
ggatgtccag attgacgttt ggcagaaact tggaaacgaa ggttggacgt ggaaagatct    480
cctaccatac tacctgaaga gtgaaaactt gacggcccct accagctctc aggttgctgc    540
tggcgctgct tataaccctg ccgtgaatgg aaaagaaggt cctctcaagg tcggctggtc    600
gggaagcctg gcctccggta atctgtcagt tgctctgaac cgtacgttcc aagccgctgg    660
tgttccatgg gttgaggatg tcaatggagg caagatgcgg ggcttcaaca tctacccatc    720
caccctcgac gttgacctca atgtccgcga agatgcagcc cgggcatact acttcccta     780
tgatgacagg aagaaccttc acctgctgga gaacaccact gccaaccgcc ttttctggaa    840
gaacggctct gctgaggaag ctattgcgga tggtgtcgag atcacctccg ctgatggcaa    900
ggtcactcgt gtgcatgcaa agaaagaggt catcatctct gctggtgccc tgcggtctcc    960
tctcattctc gagctttcag gagttggaaa cccaacgtaa gtgttccact gatgccagcc   1020
cctctctatc accgtctctg accctcgtag catcctcaaa aagaacaaca taaccccacg   1080
tgtcgatctc cccaccgttg gggagaacct ccaagaccag ttcaacaacg gcatggctgg   1140
cgaaggatac ggcgtccttg ccggtgcctc aacgtgacc taccctccca tctccgacgt    1200
cttcggtaac gagactgact ctatcgttgc atctctccga tctcaactct ccgactacgc    1260
cgccgcgacc gtcaaggtca gcaacggcca catgaagcag gaggaccttg agcgcctcta   1320
ccagctccaa tttgacctca tcgtcaagga caaggtccct atcgccgaga tcctcttcca    1380
ccccggtggt ggaaacgccg tgtcctccga attctggggc ttgcttccct tcgcccgtgg    1440
caacatccac attagctcca atgacccgac tgctcccgcc gccatcaacc ctaactactt    1500
tatgttcgaa tgggacggca agagccaggc cggtatcgcc aagtacatca ggaagattct    1560
ccgcagcgca ccattgaaca aacttattgc gaaggaaacc aagcccggtc tctctgagat    1620
tccggccact gctgcggatg agaagtgggt tgaatggctc aaggctaact gtaagttgaa    1680
tcctttcttg gcttcgatgg tgagtctgac gtgagctctc tagatcgttc aacttccac    1740
cccgtcggaa ctgctgccat gatgcctcgt tccattggtg gcgttgttga taccgtctc    1800
cgggtctatg gtaccagcaa tgttcgcgtc gtagatgcgt ctgtcctgcc cttccaggtt    1860
tgcggccact tggttagcac gctttatgcc gttgccgagc gcgcttccga cttgattaag    1920
gaggatgcga agagtgctta g                                              1941
```

<210> SEQ ID NO 3
<211> LENGTH: 1782
<212> TYPE: DNA
<213> ORGANISM: Aspergillus oryzae NBRC5375

<400> SEQUENCE: 3

```
atgctcttct cactggcatt cctgagtgcc ctgtcgctgg ccacggcatc accggctgga     60
cgggccaaga acactacgac atacgactac atcgttgtgg gaggcggcac aagtggtctt    120
```

```
gtggtcgcaa atcgcctttc tgagaaccee gatgtctccg ttcttctgct tgaggccggt      180
gcttctgtgt tcaacaaccc ggacgtaacc aacgctaacg gttatggatt ggcctttggc      240
tcggccatcg actggcagta ccagtctatt aaccaaagct atgcaggagg taaacagcaa      300
gttctgcgtg ctggtaaggc ccttggagga accagtacaa tcaatggaat ggcctatacc      360
cgcgcagagg atgtccagat tgacgtttgg cagaaacttg aaacgaagg ttggacgtgg       420 aaagatctcc taccatacta cctgaagagt gaaaacttga cggcccctac cagctctcag      480
gttgctgctg gcgctgctta taaccctgcc gtgaatggaa aagaaggtcc tctcaaggtc      540
ggctggtcgg gaagcctggc ctccggtaat ctgtcagttg ctctgaaccg tacgttccaa      600
gccgctggtg ttccatgggt tgaggatgtc aatggaggca agatgcgtgg cttcaacatc      660
tacccatcca ccctcgacgt tgacctcaat gtccgcgaag atgcagcccg gcatactac       720 ttcccttatg atgacaggaa gaaccttcac ctgctggaga acaccactgc caaccgcctt      780
ttctggaaga acggctctgc tgaggaagct attgcggatg tgtcgagat cacctccgct       840 gatggcaagg tcactcgtgt gcatgcaaag aaagaggtca tcatctctgc tggtgccctg      900
cggtctcctc tcattctcga gctttcagga gttggaaacc caaccatcct caaaagaac       960 aacataaccc cacgtgtcga tctcccacc gttggggaga acctccaaga ccagttcaac       1020
aacggcatgg ctggcgaagg atacggcgtc cttgccggtg cctcaaccgt gacctaccct      1080
tccatctccg acgtcttcgg taacgagact gactctatcg ttgcatctct ccgatctcaa      1140
ctctccgact acgccgccgc gaccgtcaag gtcagcaacg ccacatgaa gcaggaggac       1200 cttgagcgcc tctaccagct ccaatttgac ctcatcgtca aggacaaggt ccctatcgcc      1260
gagatcctct ccaccccgg tggtggaaac gccgtgtcct ccgaattctg gggcttgctt      1320
cccttcgccc gtggcaacat ccacattagc tccaatgacc cgactgctcc cgccgccatc      1380
aaccctaact actttatgtt cgaatgggac ggcaagagcc aggccggtat cgccaagtac      1440
atcaggaaga ttctccgcag cgcaccattg aacaaactta ttgcgaagga aaccaagccc      1500
ggtctctctg agattccggc cactgctgcg gatgagaagt gggttgaatg ctcaaggct       1560 aactatcgtt ccaacttcca ccccgtcgga actgctgcca tgatgcctcg ttccattggt      1620
ggcgttgttg ataaccgtct ccgggtctat ggtaccagca atgttcgcgt cgtagatgcg      1680
tctgtcctgc ccttccaggt ttgcggccac ttggttagca cgctttatgc cgttgccgag      1740
cgcgcttccg acttgattaa ggaggatgcg aagagtgctt ag                        1782
```

<210> SEQ ID NO 4
<211> LENGTH: 6
<212> TYPE: PRT
<213> ORGANISM: Aspergillus oryzae NBRC5375

<400> SEQUENCE: 4

Ala Gly Val Pro Trp Val
1               5

<210> SEQ ID NO 5
<211> LENGTH: 18
<212> TYPE: DNA
<213> ORGANISM: Aspergillus oryzae NBRC5375

<400> SEQUENCE: 5
gctggtgttc catgggtt                                                    18

<210> SEQ ID NO 6

```
<211> LENGTH: 28
<212> TYPE: DNA
<213> ORGANISM: Artificial Sequence
<220> FEATURE:
<223> OTHER INFORMATION: Synthetic construct; Primer 1

<400> SEQUENCE: 6
tgggatccta tgctcttctc actggcat                                          28

<210> SEQ ID NO 7
<211> LENGTH: 42
<212> TYPE: DNA
<213> ORGANISM: Artificial Sequence
<220> FEATURE:
<223> OTHER INFORMATION: Synthetic construct; Primer 2

<400> SEQUENCE: 7
gccaagcttc taagcactct tcgcatcctc cttaatcaag tc                          42

<210> SEQ ID NO 8
<211> LENGTH: 59
<212> TYPE: DNA
<213> ORGANISM: Artificial Sequence
<220> FEATURE:
<223> OTHER INFORMATION: Synthetic construct; Primer gene1F

<400> SEQUENCE: 8
acgcgtcgac tgaccaattc cgcagctcgt caaaatgctc ttctcactgg cattcctga       59

<210> SEQ ID NO 9
<211> LENGTH: 38
<212> TYPE: DNA
<213> ORGANISM: Artificial Sequence
<220> FEATURE:
<223> OTHER INFORMATION: Synthetic construct; Primer gene1R

<400> SEQUENCE: 9
ggctgaacta attcctccta cgcttctcac gaatcgtg                              38

<210> SEQ ID NO 10
<211> LENGTH: 36
<212> TYPE: DNA
<213> ORGANISM: Artificial Sequence
<220> FEATURE:
<223> OTHER INFORMATION: Synthetic construct; Primer 3

<400> SEQUENCE: 10
ttatgctctt ctcactggca ttcctgagtg ccctgt                                36

<210> SEQ ID NO 11
<211> LENGTH: 36
<212> TYPE: DNA
<213> ORGANISM: Artificial Sequence
<220> FEATURE:
<223> OTHER INFORMATION: Synthetic construct; Primer 4

<400> SEQUENCE: 11
gctaagcact cttcgcatcc tccttaatca agtcgg                                36

<210> SEQ ID NO 12
<211> LENGTH: 18
<212> TYPE: DNA
<213> ORGANISM: Artificial Sequence
<220> FEATURE:
<223> OTHER INFORMATION: Synthetic construct; Primer 5
```

```
<400> SEQUENCE: 12
aacccatgga acaccagc                                                18
```